(12) United States Patent
Kåberg Johard

(10) Patent No.: US 11,404,167 B2
(45) Date of Patent: Aug. 2, 2022

(54) SYSTEM FOR ANONYMOUSLY TRACKING AND/OR ANALYSING HEALTH IN A POPULATION OF SUBJECTS

(71) Applicant: BRILLIANCE CENTER B.V., Amsterdam (NL)

(72) Inventor: Leonard Kåberg Johard, Kazan (RU)

(73) Assignee: BRILLIANCE CENTER BV, Amsterdam (NL)

( * ) Notice: Subject to any disclaimer, the term of this patent is extended or adjusted under 35 U.S.C. 154(b) by 0 days.

(21) Appl. No.: 17/247,530

(22) Filed: Dec. 15, 2020

(65) Prior Publication Data

US 2021/0104332 A1    Apr. 8, 2021

Related U.S. Application Data

(63) Continuation of application No. 17/059,366, filed as application No. PCT/IB2020/057982 on Aug. 26, 2020.

(30) Foreign Application Priority Data

Sep. 25, 2019  (SE) .................................. 1900152-8
Feb. 25, 2020  (SE) .................................. 2000041-0
Jul. 28, 2020  (WO) .................. PCT/IB2020/057098

(51) Int. Cl.
*G16H 50/70* (2018.01)
*G16H 10/60* (2018.01)
(Continued)

(52) U.S. Cl.
CPC ......... *G16H 50/70* (2018.01); *G06F 21/6254* (2013.01); *G16H 10/60* (2018.01);
(Continued)

(58) Field of Classification Search
CPC ............................................... G06Q 50/22–24
See application file for complete search history.

(56) References Cited

U.S. PATENT DOCUMENTS 7,801,591 B1   9/2010 Shusterman
8,388,530 B2   3/2013 Shusterman
(Continued)

FOREIGN PATENT DOCUMENTS

GB            2549786          11/2017
KR     WO 2018/128207 A1 *   7/2018  ............. G06F 21/62
WO        2020/050760          3/2020

OTHER PUBLICATIONS

Swedish Search Report for SE 1900152-8 dated Jun. 22, 2020, 3 pages.
(Continued)

*Primary Examiner* — Robert W Morgan
*Assistant Examiner* — Edward B Winston, III
(74) *Attorney, Agent, or Firm* — Nixon & Vanderhye

(57) ABSTRACT

Systems are provided for anonymously tracking and/or analyzing transitioning, flow or movement of individual subjects between health states or health-related subject states. There is provided a system for enabling anonymous estimation of the amount and/or flow of individual subjects, referred to as individuals, in a population transitioning and/or moving and/or coinciding between two or more health states or health-related subject states. The system receives identifying data from two or more individuals; generates, online and by one or more processors, an anonymized identifier for each individual; and stores: the anonymized identifier of each individual together with data representing a health state or health-related subject state; and/or a skew measure of such an anonymized identifier.

13 Claims, 15 Drawing Sheets

(51) Int. Cl.
G16H 50/30 (2018.01)
G16H 40/20 (2018.01)
G06F 21/62 (2013.01)
G16H 50/50 (2018.01)
A61B 5/00 (2006.01)

(52) U.S. Cl.
CPC ............ *G16H 40/20* (2018.01); *G16H 50/30* (2018.01); *G16H 50/50* (2018.01); *A61B 5/7203* (2013.01)

(56) References Cited

U.S. PATENT DOCUMENTS

| | | | |
|---|---|---|---|
| 8,653,965 | B1 | 2/2014 | Otto et al. |
| 8,972,187 | B1 | 3/2015 | Steinmetz et al. |
| 9,571,510 | B1 | 2/2017 | Shen et al. |
| 10,424,406 | B2 * | 9/2019 | Jafer .................. G06F 21/6254 |
| 10,681,060 | B2 | 6/2020 | Scheidler et al. |
| 2002/0019764 | A1 | 2/2002 | Mascarenhas |
| 2007/0038863 | A1 | 2/2007 | Nguyen et al. |
| 2007/0239705 | A1 | 10/2007 | Hunt et al. |
| 2008/0065413 | A1 * | 3/2008 | Taniike .................. G16H 20/30 705/2 |
| 2008/0227063 | A1 * | 9/2008 | Kenedy .................. G16B 20/00 434/219 |
| 2011/0134240 | A1 | 6/2011 | Anderson et al. |
| 2012/0131075 | A1 | 5/2012 | Mawdsley et al. |
| 2012/0204026 | A1 | 8/2012 | Shi et al. |
| 2013/0151540 | A1 | 6/2013 | Pathak et al. |
| 2014/0063237 | A1 | 3/2014 | Stone et al. |
| 2015/0026181 | A1 | 1/2015 | Milton et al. |
| 2015/0088611 | A1 | 3/2015 | Wagenseil et al. |
| 2015/0149208 | A1 | 5/2015 | Lynch et al. |
| 2016/0364736 | A1 | 12/2016 | Maugans, III |
| 2017/0279616 | A1 | 9/2017 | Loeb et al. |
| 2017/0337397 | A1 | 11/2017 | Tang |
| 2018/0117447 | A1 | 5/2018 | Tran et al. |
| 2018/0307859 | A1 * | 10/2018 | LaFever .................. G16H 10/60 |
| 2018/0322941 | A1 * | 11/2018 | Krishnan ................ G16H 40/63 |
| 2019/0026491 | A1 | 1/2019 | Telford et al. |
| 2019/0044968 | A1 | 2/2019 | Faulkner et al. |
| 2019/0073489 | A1 | 3/2019 | Amschler et al. |
| 2019/0089711 | A1 | 3/2019 | Faulkner |
| 2019/0318813 | A1 * | 10/2019 | Gkoulalas-Divanis ...................... G16H 10/60 |
| 2020/0082290 | A1 | 3/2020 | Pascale et al. |
| 2020/0205709 | A1 * | 7/2020 | Behzadi .................. A61B 5/16 |
| 2020/0265163 | A1 | 8/2020 | Chakraborty et al. |
| 2020/0311296 | A1 | 10/2020 | Kim et al. |
| 2020/0387274 | A1 | 12/2020 | Rodriguez Bravo et al. |

OTHER PUBLICATIONS

Clifton et al., "Tools for Privacy Preserving Distributed Data Mining", ACM SIGKDD explorations newsletter, Dec. 1, 2002, vol. 4, Issue 2, pp. 28-34 (7 total pages).
Rebollo-Monedero et al., "k-Anonymous microaggregation with preservation of statistical dependence", Information Sciences, Jan. 7, 2016, vol. 342, pp. 1-23 (23 total pages).
Gupta et al., "An Exploration to Location Based Service and Its Privacy Preserving Techniques: A Survey", Wireless Personal Communications, May 12, 2017, vol. 96, pp. 1973-2007, (35 total pages).
Gramaglia et al., "Preserving Mobile Subscriber Privacy in Open Datasets of Spatiotemporal Trajectories", IEEE INFOCOM 2017—IEEE Conference on Computer Communications, May 1, 2017 (9 total pages).
Swedish Search Report for SE 2000041-0 dated Oct. 13, 2020, 4 pages.
Jin et al., "A Review of Secure and Privacy-Preserving Medical Data Sharing", IEEE Access, May 23, 2019, vol. 7, pp. 61656-61669 (14 total pages).
Ali et al., Validating Leaked Passwords with k-Anonymity, <https://blog.cloudflare.com/validating-leaked-passwords-with-k-anonymity/>, Feb. 21, 2018 (9 total pages).
Beibachir, "SmartCameras" $2010^{th}$ edition, Springer US, Dec. 2, 2009, Preface and Table of Contents (10 pages).
Gidofalvi, "Spatio-temporal Data Mining for Location-Based Services", 2007, Abstract, Acknowledgements and Table of Contents (11 total pages).
Jones et al., "Yahtzee™: An Anonymized Group Level Matching Procedure", Computer and Society, arXiv, Cornell University, Submitted Dec. 5, 2011 (19 total pages).
Nasir et al., "Privacy Preservation in Skewed Data Using Frequency Distribution and Weightage (FDW)", Journal of Medical Imaging and Health Informatics, Oct. 20, 2017, vol. 7, No. 6, p. 1-12 (12 total pages).
Shimonski, "Cyber Reconnaissance, Surveillance and Defense", Syngress, Oct. 30, 2014 (6 pages).
Wikipedia contributors, "K-anonymity", Wikipedia, The Free Encyclopedia, Sep. 5, 2019, from https://en.wikipedia.org/w/index.php?title=K-anonymity&oldid=91432376 (6 pages).
Wikipedia contributors, "Samsung Health", Wikipedia, The Free Encyclopedia, Sep. 18, 2019, from https://en.wikipedia.org/w/index.php?title=Samsung_Health&oldid=916355677 (6 pages).
Wikipedia contributors, "Smartwatch", Wikipedia, The Free Encyclopedia, Sep. 14, 2019, from https://en.wikipedia.org/w/index.php?title=Smartwatch&oldid=915584982 (12 pages).
Swedish Search Report for SE 1900174-2 dated Jun. 23, 2020, 3 pages.
Abdelhameed et al., "Privacy-preserving tabular data publishing: A comprehensive evaluation from web to cloud", Computers & Security, 2017, vol. 72, pp. 74-95 (22 total pages).
Wang et al., "Privacy-protected Social Media User Trajectories Calibration", 2016 IEEE 12th International Conference on e-Science, 2016, pp. 293-302.
International Search Report for PCT/IB2020/057098 dated Sep. 21, 2020, 7 pages.
International Search Report for PCT/IB2020/057982 dated Oct. 7, 2020, 7 pages.
International Search Report for PCT/IB2020/057783 dated Sep. 28, 2020, 7 pages.
Wikipedia contributors, "Mobile web analytics", Wikipedia, The Free Encyclopedia, Aug. 23, 2018, from https://en.wikipedia.org/w/index.php?title=Mobile_web_analytics&oldid=856152135 (5 pages).
Wikipedia contributors, "Device fingerprint", Wikipedia, The Free Encyclopedia, Sep. 18, 2019, from https://en.wikipedia.org/w/index.php?title=Device_fingerprint&oldid=856152135 (5 pages).
Firtman, "Programming the Mobile Web", Aug. 2, 2010, O'Reilly (14 pages).
Office Action issued in the co-pending U.S. Appl. No. 17/247,531 dated Apr. 27, 2021.
NIST/SEMATECH "Engineering Statistics Hanbook", NIST, DOC, 5 pages (Year 2013).
Article 29 Data Protection Working Party, "Opinion May 2014 on Anonymisation Techniques," The General Data Protection Regulation and the recommendation by the EU Article 29 WP Opinion May 2014 on Anonymization Techniques, Apr. 10, 2014, 37 pages.
European Commission, "Proposal for a Regulation of the European Parliament and of the Council concerning the respect for private life and the protection of personal data in electronic communications and repealing Directive 2002/58/EC (Regulation on Privacy and Electionic Communications)," Jan. 10, 2017, Brussels, Belgium, 40 pages.
Johard et al.,"Mind and Matter: Why It All Makes Sense," Chapter 4, Advanced Research on Biologically Inspired Cognitive Architectures, 2017, pp. 63-82.

* cited by examiner

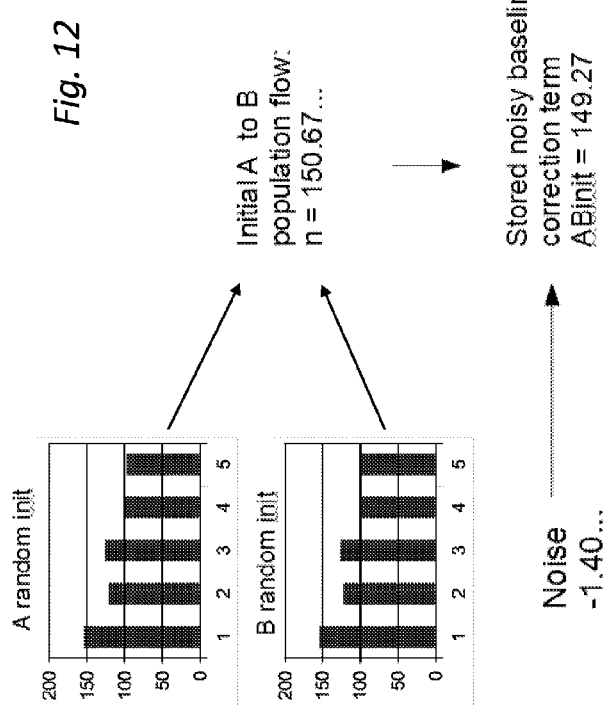

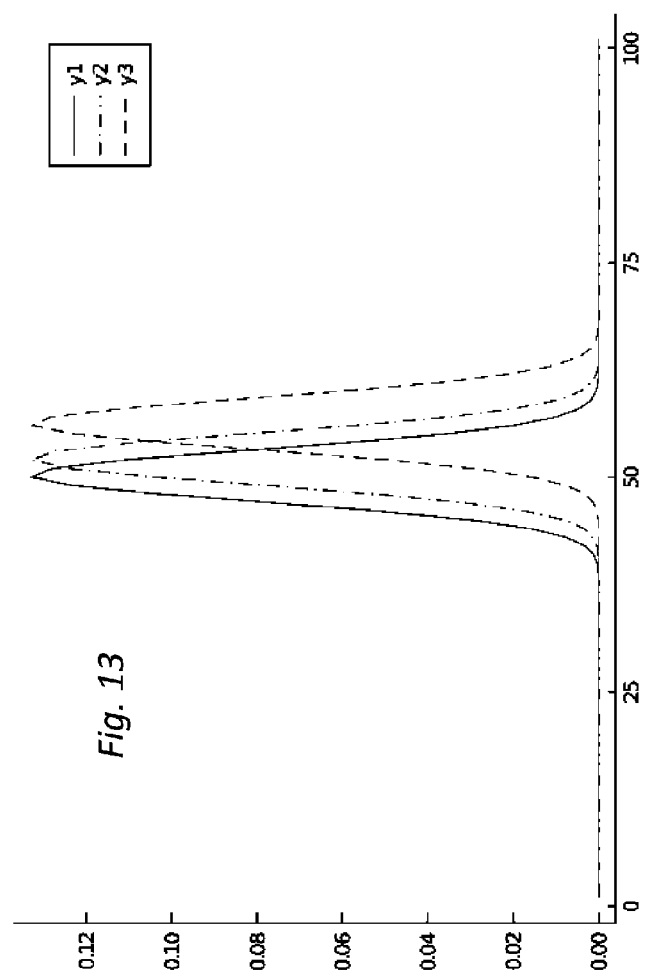

SYSTEM FOR ANONYMOUSLY TRACKING AND/OR ANALYSING HEALTH IN A POPULATION OF SUBJECTS

CROSS-REFERENCE TO RELATED APPLICATIONS

This application is a continuation of U.S. Ser. No. 17/059,366 filed Nov. 27, 2020, which was the national phase of PCT International Application No. PCT/IB2020/057982 filed on Aug. 26, 2020, under 35 U.S.C. § 371. This application also claims priority to SE 1900152-8 filed Sep. 25, 2020, to SE 2000041-0 filed Feb. 25, 2020, and to PCT/IB2020/057098 filed Jul. 28, 2020. Each of the previously noted applications is hereby incorporated by reference in their entirety.

TECHNICAL FIELD

The invention generally relates to the issue of anonymity in technological applications; and technological aspects of data collection and data/population statistics, and more specifically concerns the technical field of health monitoring and/or analysis, and especially tracking and/or estimating or measuring transitioning and/or flow between health states and/or health-related subject states and/or methods and systems and computer programs for enabling such estimation.

BACKGROUND

Legislation and public opinion increasingly drive a movement towards a right of anonymity in technology. This stands in conflicts with a need to collect data about health in populations in order to automize or optimize healthcare, medicine and public health. Pharmaceutical companies depend on health information to improve their medications and dosages, hospitals depend on similar information to improve their treatments and recommendations. New health monitoring devices rely on population data in order to create recommendations, warnings or other interventions.

Technologies that enable both data collection for statistical purposes while preserving personal anonymity is in high demand. In particular the tracking of flows of people from one point and time to another are problematic, since the reidentification of an individual at a later time is commonly the very definition of a breach of said individuals right to anonymity. This means that the whole idea of anonymous tracking of a population is somewhat counter-intuitive, since it is often practically impossible on the individual level.

Current privacy-enhancing methodologies used for tracking people that are based on pseudononymization and unique identifiers are clearly unable to fulfill these needs, which means that companies avoid collecting data on population flows at all. It is highly desirable to find any systems able to collect data on such population flows without violating anonymity. In particular, profiling is widely considered to threaten the fundamental rights and freedoms of individuals. In some cases, encryption with a very minor destruction of information has been used, so that individuals can be reidentified with sufficiently high probability (commonly with error rates of one in several tens of thousands of identifications) that any misidentification can be neglected altogether. However, such pseudonymization techniques, irrespective of whether they are or are not practically reversible, are not deemed to be compatible with the legislative interpretation of anonymization nor with public opinion of the same, since the possibility of the reidentification act itself is a defining attribute of personal data.

SUMMARY

It is a general object to provide a system for providing anonymity while calculating statistics or similar measures or estimates on health transitions (i.e. transitions between health states or health-related subject states) in a population.

It is a specific object to provide a system and method for preserving anonymity while estimating or measuring the transitioning and/or flow of individuals between two or more health states or health-related subject states It is another object to provide a system for anonymously tracking and/or analysing transition of individual subjects, referred to as individuals, between health states.

It is also an object to provide a health monitoring system or surveillance system comprising such a system.

Yet another object is to provide a computer-implemented method for enabling estimation of the amount or number, transitioning and/or flow of individuals in a population transitioning and/or coinciding between two or more health states or health-related subject states.

A further object is to provide a method for generating a measure of transitioning and/or flow and/or movement of individual subjects, referred to as individuals, between health states or health-related subject states.

Still another object is to provide a computer program and/or computer-program product and a system configured to perform such a computer-implemented method.

These and other objects are met by embodiments as defined herein.

According to a first aspect, there is provided a system comprising:
  one or more processors;
  an anonymization module configured to, by the one or more processors: receive, for each one of a multitude of individuals comprising individual subjects in a population of individuals, identifying information representative of an identity of the individual, and to generate anonymous identifier skew measures based on identifying information of one or more individuals;
  a memory configured to store at least one anonymous identifier skew measure based on at least one of the generated identifier skew measures;
  an estimator configured to, by the one or more processors: receive, from said memory and/or directly from said anonymization module, a number of anonymous identifier skew measures, at least one identifier skew measure for each of at least two health states or health-related subject states of individuals, and to generate one or more population flow measures related to individuals passing from one health state or health-related subject state to another health state or health-related subject state based on the received anonymous identifier skew measures.

According to a second aspect, there is provided a system for anonymously tracking and/or analysing transitioning and/or flow and/or movement of individual subjects, referred to as individuals, between health states or health-related subject states.

The system is configured to determine, for each individual in a population of multiple individuals, an anonymized identifier using information representative of an identity of the individual as input. Each anonymized identifier corresponds to any individual in a group of individuals, the identity information of which results in the same anonymized identifier with probabilities such that no individual generates the anonymized identifier with greater probability than the sum of the probabilities of generating the identifier over all other individuals.

The system is further configured to keep track of skew measures, one skew measure for each of two or more health states or health-related subject states, wherein each skew measure is generated based on anonymized identifiers associated with the corresponding individuals associated with a specific corresponding health state or health-related subject state.

The system is also configured to determine at least one population flow measure representative of the number of individuals passing from a first health state or health-related subject state to a second health state or health-related subject state based on the skew measures corresponding to the health states or health-related subject states.

According to a third aspect, there is provided a health monitoring system or surveillance system comprising a system according to the first or second aspect.

According to a fourth aspect, there is provided a computer-implemented method for enabling anonymous estimation of the amount, transitioning and/or flow of individual subjects, referred to as individuals, in a population transitioning and/or moving and/or coinciding between two or more health states or health-related subject states. The method comprises the steps of:

receiving identifying data from two or more individuals;
generating, online and by one or more processors, an anonymized identifier for each individual; and
storing: the anonymized identifier of each individual together with data representing a health state or health-related subject state; and/or a skew measure of such an anonymized identifier.

According to a fifth aspect, there is provided a computer-implemented method for generating a measure of transitioning and/or flow and/or movement of individual subjects, referred to as individuals, between health states or health-related subject states. The method comprises the steps of:

configuring one or more processors to receive anonymous identifier skew measures generated based on identifiers from visits and/or occurrences and/or assignments of individuals to and/or in each of two health states or health-related subject states;
generating, using said one or more processors, a population flow measure between two health states or health-related subject states by comparing the anonymous identifier skew measures between the health states or health-related subject states;
storing said population flow measure to a memory.

According to a sixth aspect, there is provided a computer program comprising instructions, which when executed by at least one processor, cause the at least one processor to perform the computer-implemented method according to the fourth aspect and/or fifth aspect.

According to a seventh aspect, there is provided a computer-program product comprising a non-transitory computer-readable medium having stored thereon such a computer program.

According to an eight aspect, there is provided a system for performing the method according to the fourth aspect and/or fifth aspect.

In this way, it is actually possible to provide anonymity while allowing data collection for and calculation of health-related statistics on populations of individuals.

In particular, the proposed technology enables preservation of anonymity while estimating or measuring the flow and/or transitioning between two or more health states.

In particular, the proposed invention allows linking data points collected at different times for statistical purposes without storing personal data.

In general, the invention provides improved technologies for enabling and/or securing anonymity in connection with data collection and statistics.

Other advantages offered by the invention will be appreciated when reading the below description of embodiments of the invention.

BRIEF DESCRIPTION OF THE DRAWINGS

The invention, together with further objects and advantages thereof, may best be understood by making reference to the following description taken together with the accompanying drawings, in which:

FIG. 12 is a schematic diagram illustrating an example of how an identifier skew measure can be made anonymous by adding noise at one or more times and how this can generate a bias compensation term.

FIG. 13 is illustrating an example of noise-masking anonymization.

DETAILED DESCRIPTION

Throughout the drawings, the same reference numbers are used for similar or corresponding elements.

For a better understanding of the proposed technology, it may be useful to begin with a brief analysis of the technical problem.

A careful analysis by the inventor has revealed that it is possible to anonymize personal data by storing a partial identity, i.e. partial information about the identity of a person that is not in itself personal data. Further, it is, perhaps surprisingly, possible to construct a (health monitoring or surveillance) system that is able to measure population flows such as health state transitions using such anonymous data even in case this anonymous data is based on factors that are not directly related to the health transitions and/or their distribution. Importantly, the proposed invention also works if the used factors are uncorrelated with the population flows and/or health transitions and/or if any estimation of their a priori distribution would be infeasible. The invention is thus applicable on general populations using almost any identifying factors (i.e. types of data) without any need for further knowledge of the underlying distributions.

The invention offers systems and methods for estimating the population flow anonymously. Also provided are three specific anonymization methods and systems suitable for enabling these purposes. In brief, two such anonymization methods, hashing and noise-masking, are based on anonymizing identifying information concerning each visits to subject states in an anonymization module, while the third method is based on anonymizing the required stored data, i.e. the identifier skew measure. These methods can also be used in combination with each other.

The invention also provides a way for using the invention without first estimating the underlying distribution through the use of a decorrelating hashing module and/or a decorrelation module and/or a decorrelating skew measure.

In the following non-limiting examples of the proposed technology will be described, with reference to the exemplary schematic diagrams of FIG. 1A to FIG. 13.

Figure 1A:
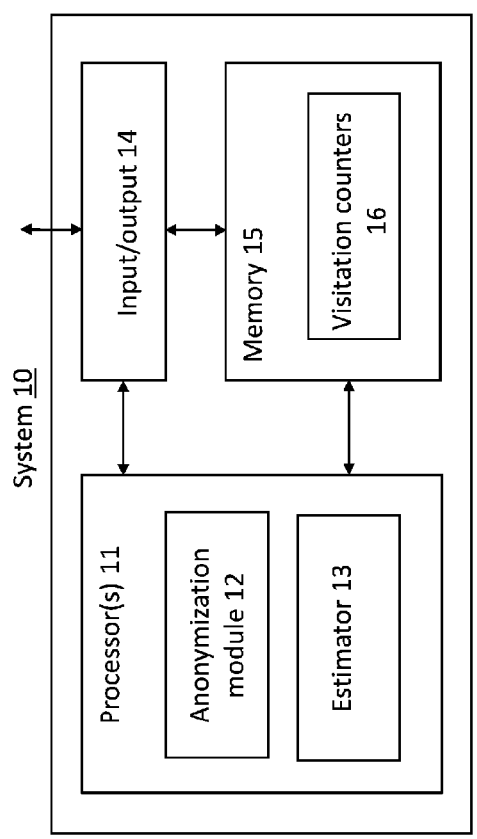
FIG. 1A is a schematic diagram illustrating an example of a system according to an embodiment.

FIG. 1A is a schematic diagram illustrating an example of a system according to an embodiment. In this particular example, the system 10 basically comprises one or more processors 11, an anonymization module 12, an estimator 13, an input/output module 14, and a memory 15 with one or more skew measures 16

According to a first aspect of the invention, there is provided a system 10 comprising:
one or more processors 11; 110;
an anonymization module 12 configured to, by the one or more processors 11; 110: receive, for each one of a multitude of individuals comprising individual subjects in a population of individuals, identifying information representative of an identity of the individual, and to generate anonymous identifier skew measures based on identifying information of one or more individuals;
a memory 15; 120 configured to store at least one anonymous identifier skew measure based on at least one of the generated identifier skew measures;
an estimator 13 configured to, by the one or more processors 11; 110: receive, from said memory and/or directly from said anonymization module, a number of anonymous identifier skew measures, at least one identifier skew measure for each of at least two subject states of individuals, and to generate one or more population flow measures (e.g. a health transition measure) related to individuals passing from one health state or health-related subject state to another health state or health-related subject state based on the received anonymous identifier skew measures.

By way of example, each identifier skew measure is generated based on two or more identifier density estimates and/or one or more values generated based on identifier density estimates.

For example, each identifier skew measure is representing the skew of the identifying information of one or more individuals compared to the expected distribution of such identifying information in the population.

In a particular example, the identifier skew measure of the anonymization module is based on a group identifier representing a multitude of individuals.

For example, the identifier skew measure may be based on a visitation counter.

By way of example, the identifier skew measure is generated based on the identifying information using a hashing function.

As an example, said one or more population flow measures includes the number and/or ratio of individuals passing from one health state or health-related subject state to another health state or health-related subject state.

For example, at least one of said one or more population flow measures is generated at least partly based on a linear transform of counter information of two or more visitation counters.

Optionally, the anonymization module 12 and/or the identifying information representative of the identity of an individual is stochastic and wherein the stochasticity of the identifying information and/or anonymization module 12 is taken into consideration when generating the linear transform.

For example, a baseline corresponding to the expected correlation from two independently generated populations is subtracted when generating the population flow measure(s).

By way of example, each identifier skew measure may be generated using a combination of the identifier and noise such that the contribution to the identifier skew measure is rendered anonymous due to a sufficient noise level for a visit to a subject state not being attributable to a specific identifier.

As an example, the identifier skew measure may be based on two or more identifier density estimates.

In a particular example, the anonymization module is configured to generate at least one identifier skew measure based on the anonymous identifier skew measure(s) stored in memory; and anonymity is provided by having added sufficient noise to the anonymous identifier skew measure stored in memory, at one or more moments, for the total contribution from any single identifier to be undeterminable.

Optionally, information about the generated noise sample(s) are also stored and used for the lowering the variance in the population flow measure.

By way of example, the identifying information representative of the identity of an individual may include and/or be based on at least one of the following non-limiting examples:
an Internet Protocol (IP) address,
a mobile phone number, device identity, user identity or subscriber identity, such as IMEI, MEID, IMSI and MSISDN.
a car license number,
biometric data originating from a subject, for example ins images, facial images, feature vectors, body images, images of uniquely identifying sets of clothing;
a MAC-address,
an identifying fingerprint of: device network layer data, device physical layer data, browser settings and/or other similar information that can be unique to a device,
a credit card number;
a ticket or access card number,
RFID,
a bar code;
home coordinates;
name;
age or day of birth;
social security number,
patient number and similar identifiers,
tax identification numbers or enumeration of an individual;
home coordinates;
a pseudonymous identifier including: a hash that reidentifies a unique person with high probability; a salted hash with discarded salt; and kept and/or discarded random and/or pseudorandom temporary identity enumeration(s) and/or hash with high probability of reidentification of a unique person,
and/or where the identity is an implicit link to a computer and the corresponding group identifier is stored as a cookie.

In a particular example, which will be elaborated on in further detail later on the anonymization module 12 is configured to generate a group identifier based on the identifying information of the individual to effectively perform microaggregation of the population into corresponding groups;
the memory 15; 120 is configured to store group identifier counters or visitation counters for each of two or more group identifiers from each of two or more health states associated with the corresponding individuals; and
the estimator 13 is configured to receive counter information from at least two group identifier counters or visitation counters, and generate one or more transition measures related to individuals passing from one health state to another health state.

For example, the anonymization module may be configured to generate a group identifier based on the identifying information of the individual by using a hashing function.

By way of example, the system 10; 100 comprises an input module 14; 140 configured to, by the one or more processors 11; 110: receive health state data, for each one of the multitude of individuals, representative of a health state, and match the health state of the individual with a group identifier counter or visitation counter corresponding to the group identifier related to the individual.

For example, each group identifier counter or visitation counter for each group identifier also corresponds to a specific health state.

According to a second aspect, there is provided a system 10; 100 for anonymously tracking and/or analysing transitioning and/or flow and/or movement of individual subjects, referred to as individuals, between health states or health-related subject states.

The system 10; 100 is configured to determine, for each individual in a population of multiple individuals, an anonymized identifier using information representative of an identity of the individual as input. Each anonymized identifier corresponds to any individual in a group of individuals, the identity information of which results in the same anonymized identifier with probabilities such that no individual generates the anonymized identifier with greater probability than the sum of the probabilities of generating the identifier over all other individuals.

The system 10; 100 is configured to keep track of skew measures, one skew measure for each of two or more health states or health-related subject states, wherein each skew measure is generated based on anonymized identifiers associated with the corresponding individuals associated with a specific corresponding health state or health-related subject state.

The system 10; 100 is also configured to determine at least one population flow measure representative of the number of individuals passing from a first health state or health-related subject state to a second health state or health-related subject state based on the skew measures corresponding to the health states or health-related subject states.

By way of example, the anonymized identifiers are group identifiers and/or noise-masked identifiers.

In a particular, non-limiting example, the system 10; 100 is configured to determine, for each individual in a population of multiple individuals, a group identifier based on a hashing function using information representative of an identity of the individual as input.

Each group identifier corresponds to a group of individuals, the identity information of which results in the same group identifier, thereby effectively performing microaggregation of the population into at least two groups.

In this example, the system 10; 100 is configured to keep track, per group, of assignment data or visitation data representing the number of assignments or visits to two or more health states by individuals belonging to the group.

The system 10; 100 is further configured to determine at least one transition measure representative of the number of individuals passing from a first health state to a second health state and/or being assigned both to the first health state and also to the second health state, based on assignment data or visitation data per group identifier.

For example, the system 10; 100 comprises processing circuitry 11; 110 and memory 15; 120, wherein the memory comprises instructions, which, when executed by the processing circuitry, causes the system to anonymously track and/or analyse flow or movement of individuals.

By way of example, the anonymization module 12 may be configured to generate a group identifier and/or noise-masked identifier based on the identifying information of the individual by using a hashing function.

Figure 1B:
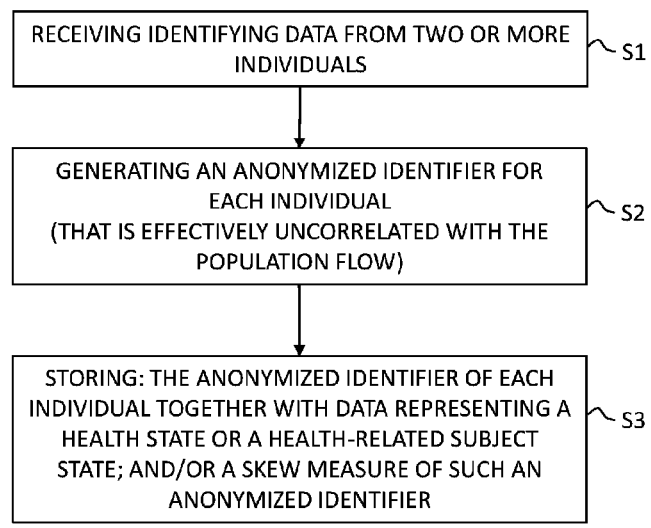
FIG. 1B is a schematic flow diagram illustrating an example of a computer-implemented method for enabling anonymous estimation of the amount, transitioning and/or flow of individual subjects, referred to as individuals, in a population transitioning and/or moving and/or coinciding between two or more health states or health-related subject states.

FIG. 1B is a schematic flow diagram illustrating an example of a computer-implemented method for enabling anonymous estimation of the amount, transitioning and/or flow of individual subjects, referred to as individuals, in a population moving and/or coinciding between two or more health states or health-related subject states.

The method comprises the steps of:
receiving (S1) identifying data from two or more individuals;
generating (S2), online and by one or more processors, an anonymized identifier for each individual; and storing (S3): the anonymized identifier of each individual together with data representing a health state or health-related subject state; and/or a skew measure of such an anonymized identifier.

For example, the anonymized identifier may be an anonymized identifier skew measure or other anonymized identifier that is effectively uncorrelated with the population flow.

By way of example, the skew measure may be decorrelating and/or the identifying data is correlated in some way with the population flow and wherein the anonymized identifier is generated with a decorrelation module and/or a decorrelating hashing module.

In a particular example, the anonymized identifier is an anonymous skew measure and the anonymized skew measure is generated based on a stored anonymous identifier skew measure to which noise has been added at one or more moments.

As an example, the anonymized identifier may be generated by adding noise to the identifying data.

By way of example, a compensation term to be added to a population flow estimate and/or necessary information for generating such a population flow estimate is calculated based on one or more generated noise sample(s) used by the method.

For example, any two stored anonymized identifiers or identifier skew measures are not linkable to each other, i.e. there is no pseudonymous identifier linking the states in the stored data.

In a particular example, the anonymized identifier is a group identifier or identity, and the group identifier or identity of each individual is stored together with data describing or representing health state; and/or a counter per health state and group identifier or identity.

By way of example, the group identifier or identity may be generated by applying a hashing function that effectively removes any pre-existing correlation between the identifying data and tendency to be assigned to one or more of the health states, and/or the generated group identifier or identity for each individual is a priori effectively uncorrelated with a transition between health states.

Optionally, activity data representative of one or more actions or activities of each individual is also stored together with the corresponding group identifier or identity and data describing health state or health-related subject state.

Figure 1C:
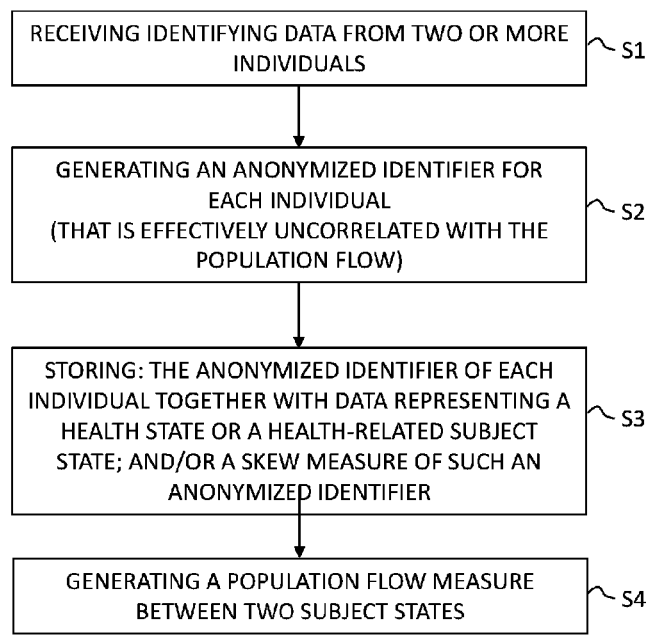
FIG. 1C is a schematic flow diagram illustrating another extended example of a computer-implemented method for enabling anonymous estimation of the amount, transitioning and/or flow of individual subjects, referred to as individuals, in a population transitioning and/or moving and/or coinciding between two or more health states or health-related subject states.

Optionally, the method may further comprise the step of generating (S4) a population flow measure between two health states or health-related subject states, as schematically indicated in FIG. 1C.

Figure 1D:
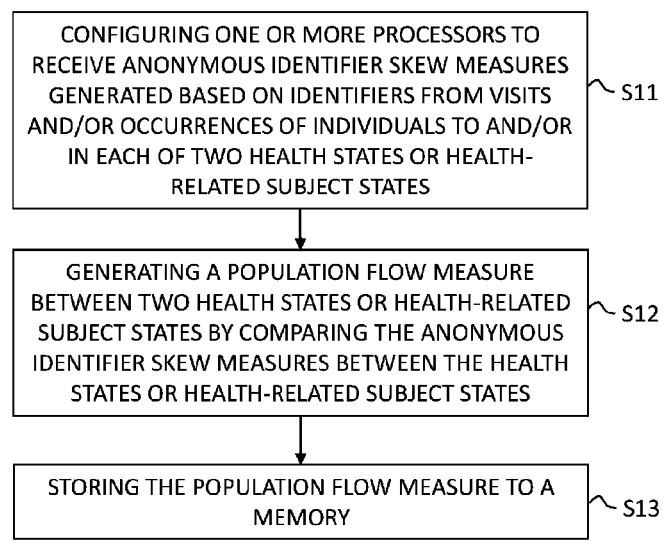
FIG. 1D is a schematic flow diagram illustrating an example of a computer-implemented method for generating a measure of transitioning and/or flow and/or movement of individual subjects, referred to as individuals, between health states or health-related subject states.

FIG. 1D is a schematic flow diagram illustrating an example of a computer-implemented method for generating a measure of transitioning and/or flow and/or movement of individual subjects, referred to as individuals, between health states or health-related subject states.

The method comprises the steps of:
configuring (S11) one or more processors to receive anonymous identifier skew measures generated based on identifiers from visits and/or occurrences and/or assignments of individuals to and/or in each of two health states or health-related subject states;
generating (S12), using said one or more processors, a population flow measure between two health states or health-related subject states by comparing the anonymous identifier skew measures between the health states or health-related subject states;
storing (S13) said population flow measure to a memory.

For example, the anonymous identifier skew measures may be counters of group identifiers or identities.

Normally, a single visitor present in one health state or health-related subject state cannot be reidentified in another health state or health-related subject state with high probability using the anonymous identifier skew measures.

For example, by high probability is meant a probability of at least 95%, or at least 99%, or at least 99.9%.

By way of example, the generating step S12 is not based on data already containing some measure of the population flow between the locations on an individual level and/or microaggregated level.

For example, the anonymous identifier skew measures are effectively uncorrelated with the population flow.

Optionally, the population flow estimate is generated based on a linear mapping from the anonymous identifier skew measures.

By way of example, the population flow measure may also be generated based on information about noise samples used to anonymize the data.

As an example, the configuring step S11 includes configuring one or more processors to receive counters of anonymous and approximately independently distributed group identities originating from visits and/or assignments of individuals to each of two health states or health-related subject states; and the generating step S12 includes generating a population flow measure such as a health transition measure between two health states or health-related subject states using a linear correlation between counters of group identifiers or identities for each of the two health states or health-related subject states.

By way of example, as an optional add-on, the health states may additionally be related to tempo-spatial locations.

Optionally, an anonymous identifier or identifier skew measure for each health state or health-related subject states may be based on two or more identifier density estimates.

Figure 2:
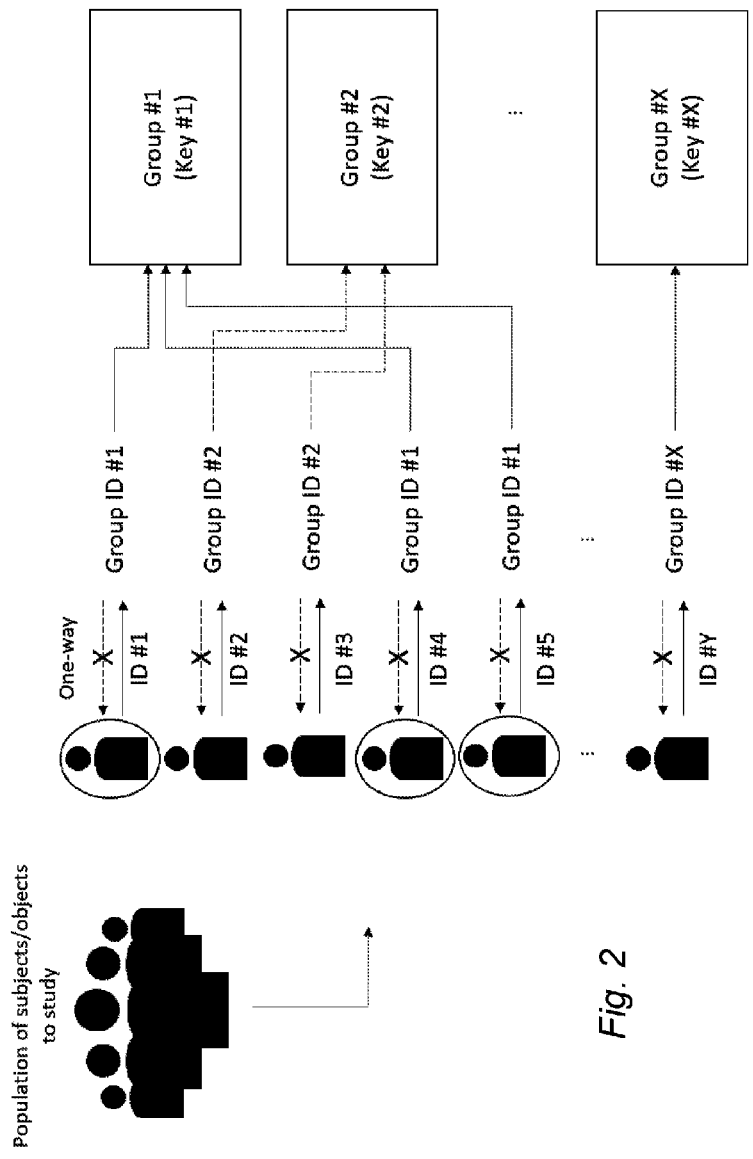
FIG. 2 is a schematic diagram illustrating an example of micro-aggregation of a population into groups.

FIG. 2 is a schematic diagram illustrating an example of micro-aggregation of a population into groups. By way of example, a population of subjects/objects under study may be micro-aggregated into groups by using suitable one-way hashing. In short, a basic idea is to use, for each one of a multitude of individuals, identifying information (such as ID #1, ID #2, ID #Y) representative of an identity of the individual, and generate a group identifier (Group ID #1, . . . Group ID #X) based on the identifying information of the individual to effectively perform micro-aggregation of the population into corresponding groups (Group #1, . . . Group #X).

Figure 3:
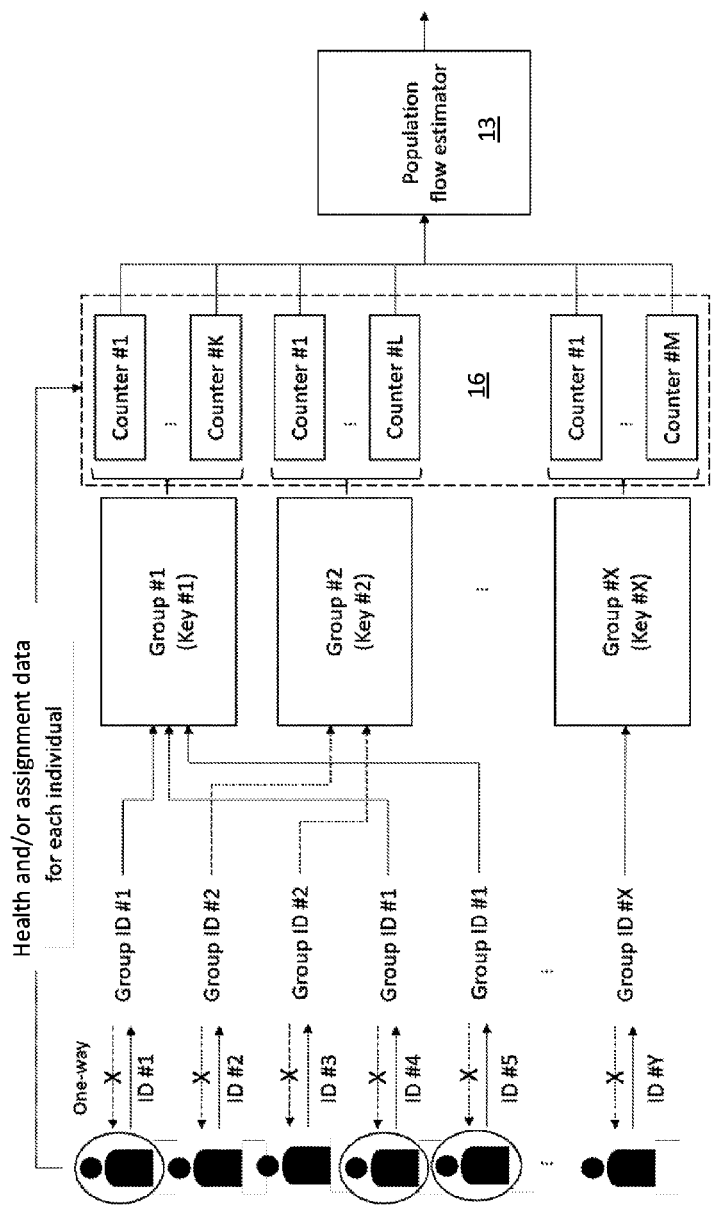
FIG. 3 is a schematic diagram illustrating another example of micro-aggregation of a population into groups, including the concept of group identifier counters and/or skew measures.

FIG. 3 is a schematic diagram illustrating another example of micro-aggregation of a population into groups, including the concept of visitation counters. There are visitation counters 16 for each of two or more group identifiers from each of two or more tempo-spatial locations or localities associated with the corresponding individuals. In other words, each of at least two groups (with corresponding group identifiers) has a number (K, L, M) of visitation and/or group identifier counters for maintaining counts from each of two or more health states or health-related subject states associated with the corresponding individuals of the considered group.

The estimator 13, also referred to as a population flow or health transition estimator, may then be configured to receive counter information from at least two visitation counters or group identifier counters, and generate one or more population flow measures such as health transition measures related to individuals passing from one health state to another health state.

Figure 4:
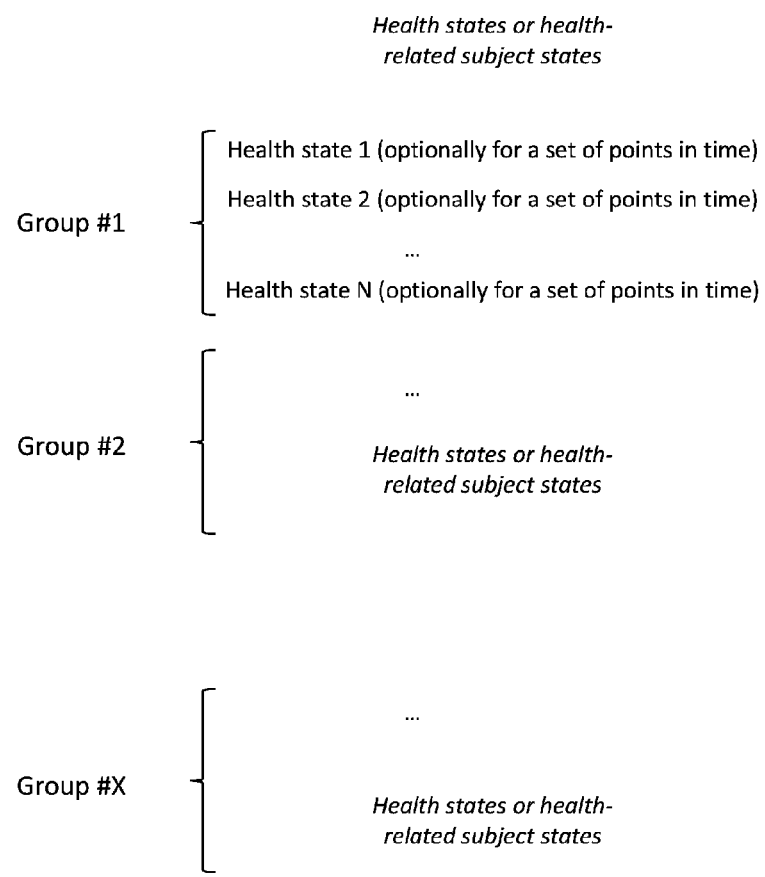
FIG. 4 is a schematic diagram illustrating how each group of individuals may be associated with a set of health states N, optionally each for a set of points in time.

FIG. 4 is a schematic diagram illustrating how each group of individuals may be associated with a set of health states N, optionally each for a set of points in time.

Optionally, the system 10 comprises an input module 14 configured to, by the one or more processors: receive location data, for each one of the multitude of individuals, representative of a health state, and match the health state of the individual with a visitation or group identifier counter 16 corresponding to the group identifier or group identity related to the individual.

For example, each visitation counter or group identifier counter 16 for each group identifier also corresponds to a specific health state.

By way of example, the one or more population flow measures such as health transition measures includes the number and/or ratio of individuals passing from one health state to another health state.

In a particular example, at least one of said one or more population flow measures such as health transition measures is generated at least partly based on a linear transform of the counter information of two or more visitation counters or group identifier counters.

For example, the anonymization module 12 and/or the identifying information representative of the identity of an individual may be stochastic, and the stochasticity of the identifying information (identifier) and/or anonymization module 12 may be taken into consideration when generating the linear transform.

As an example, the linear transform may be at least partly based on a correlation between two visitation or group identifier counters and from which a baseline corresponding to the expected correlation from two independently generated populations is subtracted.

Figure 5:
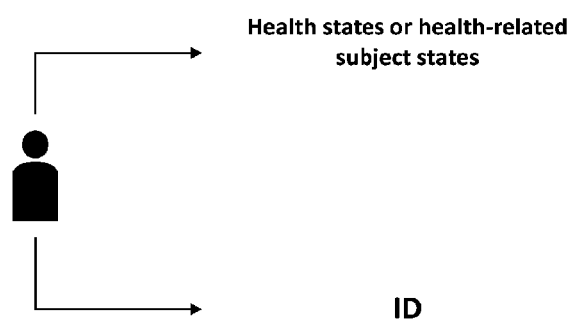
FIG. 5 is a schematic diagram illustrating examples of health state data and useful identifying information (ID).

FIG. 5 is a schematic diagram illustrating an example of the association of health state data and useful identifying information (ID).

Non-limiting examples of identifying information, also called an identifier, representative of the identity of an individual may include and/or be based on at least one of:
  an Internet Protocol (IP) address,
  a mobile phone number, device identity, user identity or subscriber identity, such as IMEI, MEID, IMSI and MSISDN.
  a car license number,
  biometric data originating from a subject, for example ins images, facial images, feature vectors, body images, images of uniquely identifying sets of clothing;
  a MAC-address,
  an identifying fingerprint of: device network layer data, device physical layer data, browser settings and/or other similar information that can be unique to a device,
  a credit card number;
  a ticket or access card number,
  RFID
  bar codes;
  home coordinates;
  name;
  age or day of birth;
  social security number,
  patient number and similar identifiers,
  tax identification numbers or enumeration of individuals;
  pseudonymous identifiers including: hashes that reidentify a unique person with high probability; salted hashes with discarded salts; and kept and/or discarded random and/or pseudorandom temporary identity enumerations and/or hashes with high probability of reidentification of a unique person; and/or
  the identity may be an implicit link to a computer and/or other memory and/or the corresponding group identifier and/or noise-masked identifier may be stored in a file, i.e. a cookie.

This means one or more of the above information items and/or a combination thereof.

In a particular example, the anonymization module is configured to operate based on a random table, a pseudo-random table, a cryptographic hash function and/or other similar function that is effectively uncorrelated with the aspect of interest the system is designed to study.

As an example, the hashing process may be non-deterministic.

By way of example, it may be considered important that data of at least two individuals is collected or expected to be collected per unique group identifier when such are used. Alternatively, with a slightly weaker criterion, it may be important that at least two individuals are expected to exist in some population that can reasonably be expected to visit the subject state, e.g. individuals in the city or country of interest where the data is being collected. This also applies to devices when such are used. The range of reasonable identities would be the criterion for anonymity, not the range of reasonable identifiers. For example, the range of possible phone numbers is generally larger than the range of possible people in a country.

More generally, to handle the case of noise-based anonymization with a similar criterion, it may for example be important that the probability of correctly identifying an individual should be no higher than 50%), with possible optional exceptions for situations with negligible probability. It may for example additionally be important that the probability of identifying a person is no higher than 50% when given a known subject state and/or reasonably available information about such subject states where a specific person is present. Such knowledge may also be probabilistic. Such probabilities can be calculated in a straightforward manner by the skilled person using analytical or Monte Carlo methods.

When using a noise-masked identifier, it may for example be important that no noise-masked identifier value is linkable to any single person with a probability higher than that of the identifier value belonging to any of the other people in the population. As a consequence, the probability of it belonging to any of the n−1 remaining individuals in the population of n people should ideally be above 0.5. In other words, the probability of identifying an individual should not be above 0.5 and in many cases much lower for it the offer similar protection to k-anonymization for some k=2 or higher. In other words, each of this multitude of identifiers should have a probability of generating the given noise-masked identifier value that is smaller than the sum of the probabilities of generating the noise-masked identifier from each other identifier. If the noise level is too low, the collected data allows the creation of profiles and the method is no longer anonymous due to insufficient data collection.

As an example, the probabilities of generating some specific noise-masked identifier might be 0.6, 0.4, 0.3 and 0.4 for four different received identifiers, with the greatest probability being 0.6/1.7 of the data correctly assigned to a specific individual and thus achieving an anonymity greater than 0.5. It is most often reasonable to assume that that the a priori probability is identical across the population. In other cases, for example if people are identified by IP address and certain ranges of IP addresses are a priori known to be more likely to be unused, the a priori distribution need to be taken into consideration. This is often a very difficult estimation to make in practice. In such cases, it would be desirable to instead use a decorrelation module and/or have probabilities that have distributions that are sufficiently distributed to leave ample margin for uncertainties in the a priori probability. A completely even distribution across all possible noise-masked identifier values, regardless of received identifier, is not practical, as this would clearly remove any desirable expected skew in the data caused by a particular set of identifiers being used to generate the noise-masked identifiers. In other words, picking a suitable noise distribution becomes a balance between accuracy in the estimation and provided anonymity. There is, however, usually a wide range of choices that can provide both a high degree of anonymity and reasonable accuracy.

It should be noted that the criterion/criteria for anonymity comprises not just the fact that the original identifier can no longer be recreated with a high probability, e.g. to prevent identification of the MAC/IP addresses, facial images etc. This weaker property is true for some salted hashes, temporary random identifiers and a large range of other similar identifiers referred to as pseudonymous. Our invention instead targets a significantly stricter level of anonymization by also preventing the linking of data, for example into profiles, by making an attacker unable to link two or more data points using the stored identifiers on the individual level (while still enabling linking on the aggregated, statistical level). This is also the common definition of anonymization in modern and stricter definition provided by recent scientific and legal definitions of anonymity, such as the General Data Protection Regulation and the recommendation by the EU Article 29 WP Opinion May 2014 on Anonymization Techniques (with the specific criteria: "is it still possible to link records relating to an individual?"). In contrast, any availability or possibility of non-anonymous data linkable on an individual level, e.g. pseudonymous identifiers, would make the objective trivial to achieve and nonsensical to achieve in the manner described by the invention.

For example, one particular effect of anonymization described herein can be to effectively prevent or significantly hinder any potential profiling of individuals by a third party using the data stored in the system.

As an alternative to methods and/or systems of the invention, data can be anonymized after collection while preserving the population flow measure in various ways, for example by microaggregating the population and storing the population flow per group. However, such anonymization requires one or more non-anonymous data collections step. As such, such a system and/or method for population flow measure would not be anonymous, as it would require the collection and storage of personal data from each individual at least for the period separating the visits to the corresponding subject states. This problem is also important enough to be recognized explicitly in legislation, for example in the preamble of the "Proposal for a REGULATION OF THE EUROPEAN PARLIAMENT AND OF THE COUNCIL concerning the respect for private life and the protection of personal data in electronic communications and repealing Directive 2002/58/EC (Regulation on Privacy and Electronic Communications)" where it is stated:

"To display the traffic movements in certain directions during a certain period of time, an identifier is necessary to link the positions of individuals at certain time intervals. This identifier would be missing if anonymous data were to be used and such movement could not be displayed.".

These conclusions did clearly not foresee the invention and clearly states the perceived impossibility in achieving the stated objective with conventional methods while maintaining a proper anonymity.

Such non-anonymous data is not compatible with the data collection envisioned by the invention due to its lack of anonymity in both its collection and storage, making such data types incompatible with the objective of anonymous tracking and/or analysing movement of individual subjects.

The original identifiers might have an uneven distribution. This is the case, for example, by having ranges of MAC-addresses tied to specific vendors, by the local geographical bias of biometrically relevant phenotypes in a population or by allowing users a choice of online identifier. In such cases, the required uniform noise level may be prohibitively high. An improved and proper noise level to guarantee anonymity may need to become dependent on the identifier itself, e.g. adding more noise to identifiers that are more likely to have few neighbors, but this requires an estimation of the underlying distribution of identifiers. Such estimation of the distribution can be very difficult in practice and may also suffer from estimation errors that threaten the anonymity.

We propose, for such cases, an optional additional decorrelation module that is designed to effectively remove any relevant correlations in the anonymized identifiers. For example, it uses a cryptographic hash and/or similar decorrelating function before adding the noise to the resulting decorrelated identifier in the anonymization module. The role of the decorrelation module is to remove any patterns and/or any large-scale patterns in the distribution, which will even out the identifier density, while the anonymity is provided by the noise in the anonymization module rather than the decorrelation. In contrast to the hashing function used to generate group identifiers, the decorrelation module itself does not need to provide anonymous identifiers. Consequently, the decorrelation module may also be truly or probably reversible, such as a reversible mapping or a salted hash that allows data linking and/or a recreation of the original identifier with some probability. Further descriptions of the decorrelation aspect and possible uses of locality-sensitive hashing in a decorrelation module follows the guidelines provided in the related examples below.

In an alternative example embodiment of the decorrelation module, the decorrelating function is instead applied to the noise. This means that a noise source, typically well-behaved such as a Gaussian noise, is transformed into a decorrelated noise, i.e. one with a probability distribution effectively lacking large-scale continuous patterns, for example by applying a hashing function on the well-behaved noise. This decorrelated noise from such a decorrelation module can then be used to simultaneously anonymize and decorrelate the identifying data, for example by adding decorrelated noise and then applying a modulo rspan operation, where rspan is the range of image of the noise source. Care need to be taken in setting the numerical resolution of the noise and/or in designing the hashing method used so that the noise is not perfectly uniformly distributed, since a non-uniform distribution is needed to create the necessary identifier-related skew used by the invention.

As an alternative to the decorrelation module, a decorrelating skew measure can be used. This can for example be any skew measure that does not display large-scale patterns likely to correlate with physical systems, for example by being based on functions such as a randomly initialized table and/or function that is an effectively random identifier-dependent weighting and/or a function only maintaining small-scale patterns unlikely to give rise to significant correlation, such as a modulo operation. The necessary considerations in designing a decorrelating skew measure is largely similar to those in designing a decorrelation module and will be obvious to the skilled person.

Decorrelation of identifying data should be interpreted in context of the skew measure. If the skew measure is likely to be affected by the existing visitation probability patterns in the identifying data, for example with the identifiers affecting a specific identifier density measure on average being significantly more likely to visit a subject state than other identifiers in the population, then the visitation frequency of the identifying data can be considered correlated (with the shape of the skew measure). Hence the correlation can be broken either by breaking their correlation by changing the skew measure and/or the anonymous identifier, while the visitation frequency per subject state and identifier can be considered a given value for a measurement system. For example, since the probability of two completely random functions and/or distribution being significantly correlated is low, a pick of any random mapping would be sufficient to decorrelate them with a high probability.

Very briefly, the theoretical reason for the effectiveness of decorrelation is related to the fact that data with origin in the physical world and/or functions used to model such (e.g. most common and named functions used in engineering) form an infinitesimal and particular subset of all possible functions and have a relatively high probability of similarity and displaying spurious correlations, especially for large patterns. Small-scale physical patterns tend to be at least partly chaotic and effectively random. Further details on such properties can be found in earlier published work by the inventor (e.g. "Mind and Matter: Why It All Makes Sense"). In contrast, an effectively randomly chosen function/distribution from all possible functions/distributions has a much lower, often zero or negligible, probability of displaying such correlations with both functions of physical origin and/or other randomly chosen functions. The avalanche effect gives a different, and yet similar, perspective on the decorrelation aspect. For example, a bent function and/or those fulfilling the strict avalanche criterion can be suitable as a function for decorrelating purposes, while for example functions considered particularly well-behaved and/or functions with low-valued derivatives are usually less suitable due to their approximate linearity correlating with the approximate linearity inherent in most physical systems and models on some scale. Both cryptographic hash functions and random mappings, such as random tables, benefit from these properties but many other functions also possess and/or approximate (e.g. LSH) the relevant properties for the purpose of the invention. Suitable alternatives should be obvious to the skilled person familiar with the theory of hashing, cryptography and compression.

Note that we use adding noise herein in the general sense as the application of any stochastic mapping, not necessarily relying on the addition of a noise term to the identifier. For example, multiplicative noise may also be used. This can still be seen, form the perspective of information theory, as an addition of noise to the information encoded in the data regardless of the form of such an encoding.

The choice of specific hashing and/or noise-masked identifier may be different between the health states and may also depend on other factors. For example, certain identifiers may be assigned to hashing and others to noise-based masking. Noise may be identifier-dependent and/or dependent on the health state.

In some contexts, some accessible identifying data is considered an identifier and other potentially identifying data is considered to be additional data unknown to an attacker. For example, precise location data in a public place cannot be used to identify a person unless the attacker is likely to have location data with the same time stamps. If such data is likely to be available to the attacker, it might be suitable to additionally anonymize any additional data together with the identifier. The invention can be used in any such combination. For example, the IMEI can be used as an identifier and an anonymized identifier stored by the invention. Together with the IMEI location data is stored in order to analyze travel patterns. This additional location data may then be anonymized separately, for example by quantization of location and time into sufficiently large intervals to be rendered anonymous. The resolution may be different in residential areas and in public spaces, such as retail locations.

In general, the proposed invention can be applied to any sufficient identifying part, i.e. identifying in itself, of the identifying data and the additional identifying data may be anonymized by separate methods. The health states can then be linked statistically by those identifiers handled by the invention, while the remaining identifying data can be anonymized in a way that does not allow statistical linking of this kind.

According to another aspect, there is provided a system for anonymously tracking and/or analysing transitioning, flow and/or movement of individual subjects, referred to as individuals between health states or health-related subject states.

In this non-limiting example, the system is configured to determine, for each individual in a population of multiple individuals, a group identifier based on a hashing function using information representative of an identity of the individual as input. Each group identifier corresponds to a group of individuals, the identity information of which results in the same group identifier, thereby effectively performing microaggregation of the population into at least two groups.

Noise-masked identifiers perform the same function by adding a random noise with a distribution such that each possible noise-masked identifier value is achievable by a multitude of identifiers.

The system is further configured to keep track, per group, of visitation and/or assignment data representing the number of visits and/or assignments to two or more health states or health-related subject states by individuals belonging to the group. More generally, the system is configured to keep track of a skew measure for two or more health states or health-related subject states.

The system is also configured to determine at least one population flow measure (for the whole population) such as at least one transition measure of the number of individuals passing from a first health states or health-related subject states to a second health states or health-related subject states based on visitation data and/or assignment per group identifier.

More generally, the system is configured to determine at least one population flow measure (for the whole population) of the number of individuals passing from a first health state or health-related subject state to a second health state or health-related subject state based on the skew measure.

Figure 10:
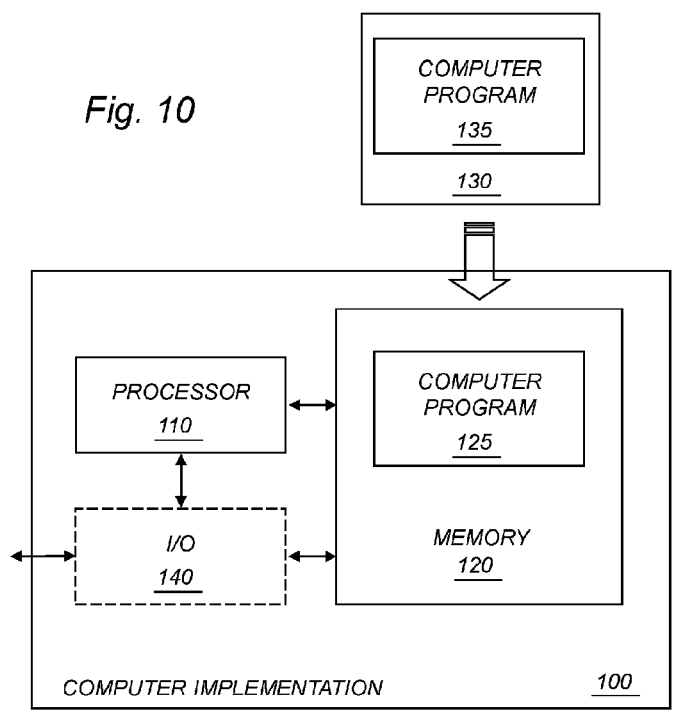
FIG. 10 is a schematic diagram illustrating an example of a computer-implementation according to an embodiment.

With exemplary reference to FIG. 1A and/or FIG. 10, the system may comprise processing circuitry 11; 110 and memory 15; 120, wherein the memory 15; 120 comprises instructions, which, when executed by the processing circuitry 11; 110, causes the system to anonymously track and/or analyse transitioning, flow and/or movement of individuals between health states.

Figure 6:
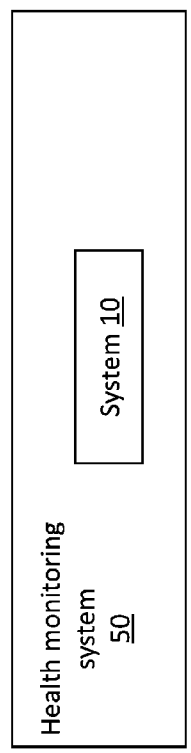
FIG. 6 is a schematic diagram illustrating an example of a health monitoring system or surveillance system.

According to yet another aspect, the proposed technology provides a health monitoring or surveillance system 50 comprising a system 10 as described herein, as schematically illustrated in FIG. 6.

Figure 7:
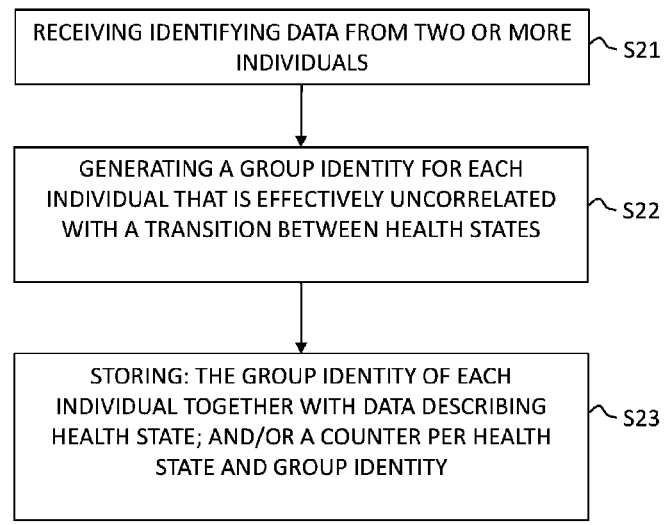
FIG. 7 is a schematic flow diagram illustrating an example of a computer-implemented method for enabling estimation of the amount or number, ratio and/or rate of individuals in a population transitioning and/or coinciding between two or more health states.

FIG. 7 is a schematic flow diagram illustrating an example of a computer-implemented method for enabling estimation of the amount or number, ratio and/or rate and/or flow of individuals in a population transitioning and/or moving and/or coinciding between two or more health states.

Basically, the comprises the steps of:

S21: receiving identifying data from two or more individuals;

S22: generating, by one or more processors, a group identifier or identity and/or noise-masked identifier for each individual that is effectively uncorrelated with the population flow and/or the transition between health states; and S23: storing: the group identifier or identity and/or noise-masked identifier for each individual together with data describing health state; and/or a (group identifier) counter per health state and group identifier or identity.

By way of example, the group identifier or identity may be generated by applying a hashing function that effectively removes any pre-existing correlation between the identifying data and tendency to be assigned to one or more of the health states.

Optionally, the noise-masked anonymization comprises a decorrelation step that effectively removes correlations in the identifier space.

For example, the population of individuals being measured may be an unknown sample from a greater population, with the greater population being large enough that the expected number of individuals in this greater population that would be assigned to each group identifier or identity and/or noise-masked identifier is two or more.

The population of individuals can for example be considered a representative sample from this greater population that may implicitly and/or explicitly also be measured through the data collected from the considered population.

Optionally, the generation of group identifier or identity may be partly stochastic each time it is applied.

By way of example, the identifying data may include, per individual, information representative of the identity of the individual. Non-limiting examples of such information may include and/or be based on at least one of:
- an Internet Protocol (IP) address,
- a mobile phone number, device identity, user identity or subscriber identity, such as IMEI, MEID, IMSI and MSISDN.
- a car license number,
- biometric data originating from a subject, for example ins images, facial images, feature vectors, body images, images of uniquely identifying sets of clothing;
- a MAC-address,
- an identifying fingerprint of: device network layer data, device physical layer data, browser settings and/or other similar information that can be unique to a device,
- a credit card number;
- a ticket or access card number,
- RFID
- bar codes;
- home coordinates;
- name;
- age or day of birth;
- social security number,
- patient number and similar identifiers,
- tax identification numbers or enumeration of individuals;
- pseudonymous identifiers including: hashes that reidentify a unique person with high probability; salted hashes with discarded salts; and kept and/or discarded random and/or pseudorandom temporary identity enumerations and/or hashes with high probability of reidentification of a unique person;
- and/or the identity may be an implicit link to a computer and/or other memory and/or the corresponding group identifier and/or noise-masked identifier may be stored in a file, i.e. a cookie.

Figure 8:
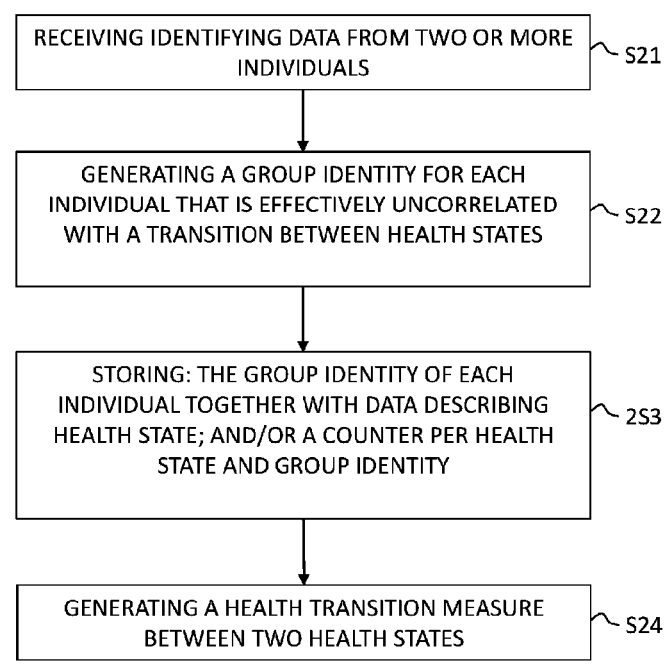
FIG. 8 is a schematic flow diagram illustrating another example of a computer-implemented method for enabling estimation of the amount or number, ratio and/or rate of individuals in a population transitioning and/or coinciding between two or more health states.

FIG. 8 is a schematic flow diagram illustrating another example of a computer-implemented method for enabling estimation of the amount or number, ratio and/or rate of individuals in a population transitioning and/or coinciding between two or more health states.

In this particular example, the method further comprises the step of:

S24: generating a population flow measure such as a health transition measure between two health states using counters of group identities for each of the two health states.

For example, the generation of the population flow may be based on a linear transform of the visitation or group identifier counters.

Optionally, the linear transform may include a correlation between a vector describing the population flow per group identifier or identity in the first health state and a vector describing the population flow per group identifier or identity in the second health state.

As an example, a baseline is subtracted from the correlation that corresponds to the expected correlation between the two vectors.

For example, the number of individuals in the population may be two or more per group identifier or identity.

Optionally, activity data representative of one or more actions or activities of each individual may also be stored together with the corresponding group identifier or identity and data describing health state, enabling analysis and understanding not only of direct health state aspects but also of actions or activities of individuals. It may also be possible to store tempo-spatial data defining temporal and/or spatial aspects such as time and/or place of an individual in a given health state.

Figure 9:
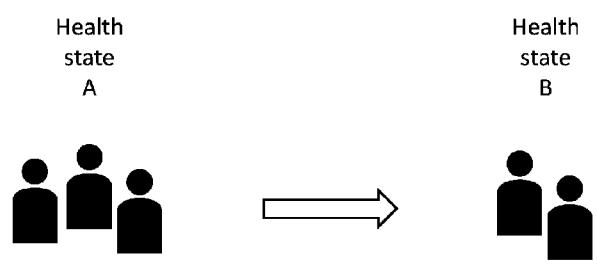
FIG. 9 is a schematic diagram illustrating an example of transitioning of one or more individuals from health state A to health state B.

FIG. 9 is a schematic diagram illustrating an example of transition or flow of one or more individuals from health state A to health state B.

Figure 11:
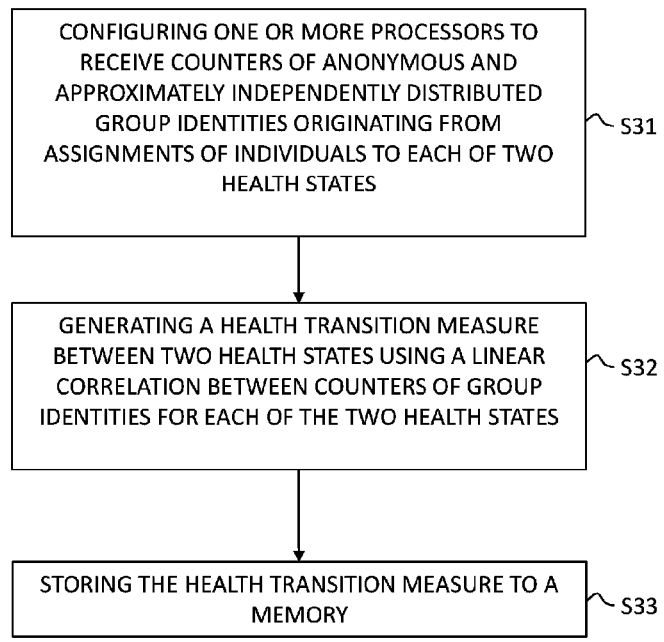
FIG. 11 is a schematic flow diagram illustrating an example of a computer-implemented method for generating a measure of transition, flow and/or movement of individual subjects, referred to as individuals, between health states.

FIG. 11 is a schematic flow diagram illustrating an example of a computer-implemented method for generating a measure of transitioning, flow and/or or movement of individual subjects, referred to as individuals, between health states.

Basically, the method comprises the steps of:

S31: configuring one or more processors to receive counters of anonymous and approximately independently distributed group identities originating from visits and/or assignments of individuals to each of two health states;

S32: generating, using said one or more processors, a population flow measure such as a health transition measure between two health states using a linear correlation between counters of group identities for each of the two health states; and S33: storing said population flow measure (e.g. a health transition measure) to a memory.

For a better understanding, various aspects of the proposed technology will now be described with reference to non-limiting examples of some of the basic key features followed by some optional features.

The invention receives some identifying data that is able to, with a high probability, uniquely identify an individual and/or personal item of an individual. Such data can be discrete numberings, for example MAC-addresses, IP addresses, license plate numbers, bar codes or random numbers stored in a cookie file. It may alternatively be continuous data, for example home coordinates, biometric measurements or a floating-point measurement identifying some unique characteristic of a personal device. It may also be types of personal data such as tax identification numbers, social security numbers, names, home addresses and phone numbers. It may also be any combination and/or function of such data from one or more sources. Depending on definition used, this identifying data may be similar to concepts such as identifiers and/or quasi-identifiers.

In preferred examples, the invention comprises an anonymization module, that comprises a (anonymizing) hashing module and/or a noise-based anonymization module.

Examples—Hashing Module

Some aspects of the invention involve a hashing module. A hashing module, in our sense, is a system that is able retrieve identifying data and generate some data about a person's identity that is sufficient to identify the individual to some group that is substantially smaller than the whole population, but not sufficiently small to uniquely identify the individual. This effectively divides the population into groups with one or more individuals, i.e. it performs an automatic online microaggregation of the population. These groups should ideally, but not necessarily, be independent from the population flows being studied in order to simplify the measurement. In other words, we seek to divide them in such a way that the expectation of the flow of each group should be approximately the same. In particular, the variance in any pair of groups should be approximately independently distributed. Expressed differently, we would like to be able to consider the group as an effectively random subset of the population in our statistical estimates. For example, this can be achieved by applying cryptographic hash or other hash that has a so-called avalanche effect. A specific example of a suitable hash, if locality-sensitivity is not desired, is a subset of bits of a cryptographic hash, such as SHA-2, of a size suitable to represent the desired number of groups that correspond to the number of individuals we would like to have per group. Padding with a constant set of bits can be used in this example to reach necessary message length. However, this specific example of hash brings some overhead to the computational requirements and hashing modules better adapted for this specific purpose can also be designed, as the application herein does not necessitate all the cryptographic requirements.

Preferably, any correlation, whether linear or of another type, that could significantly bias the resulting measure from the system should effectively be removed by the hashing module. As an example, a sufficient approximation of a random mapping, such as a system based on block ciphers, chaotic systems or pseudorandom number generation, can achieve this goal. In the minimalistic extreme, a simple modulo operation may be sufficient if this is deemed unlikely to create correlated identities.

If the identifiers do not contain such correlation, e.g. if they are randomly assigned, then the hash does not benefit from being decorrelating, as any group assignment will be effectively random even without it.

In some aspects of the invention, depending on the required conditions for anonymity, the amount of groups may be set so that either an expected two or more people from the population whose data has been retrieved or two or more people from some greater population, from which the population is effectively a random sample, is expected to be assigned to each group. The invention allows an efficient unbiased estimation in both of these cases as well as more extreme anonymizing hashing schemes with a very large number of individuals per group.

The hash key, representing a group identity, can be stored explicitly, for example a number in a database, or implicitly, for example by having a separate list per hash key.

In other words, the hashing module takes some identifying data of a population and also generates, for example, effectively (i.e. an approximation sufficiently good for the purposes herein) randomly sampled subgroups from the whole population. The hashing module as described herein has several potential purposes: ensuring/guaranteeing the decorrelation of data from the population flow (i.e. using a group identity that has, possibly unlike the identifying data, effectively no correlation with the population flow) and anonymizing the data by microaggregating it while preserving some limited information about the identity of each individual. In some embodiments of the invention the hashing module may also, as described in more detail below, serve to preserve limited information about the data itself by using a locality-sensitive hashing.

For these aspects of the invention, the statistics collected per group identity are instrumental in generating the population flow statistics for the (whole) studied population comprising a multitude such groups. The purpose of the invention is not to measure the differences between the groups as such, and in particular if the decorrelation is intentionally generating rather meaningless subdivisions of the population due to the effective removal of any potential correlations between members of the group.

As an example of suitable hashing modules, divisions into group based on continuous ranges of one or more of many meaningful variables, such as yearly incomes, home location, IP-range or height are unsuitable criteria in the preferred embodiment, as this is likely to results in different expected population flow patterns for each group that would need to be estimated for the overall population flow to be measured. On the other hand, we could use, for example, a limited number of bits from a cryptographic hash or a random mapping from an initial grouping into sufficiently small ranges of any of these criteria(s) in order aggregate an effectively random selection of such small groups of continuous ranges into a larger group. In other words, we divide the identifiers into many small continuous ranges and define our groups as some effectively random selection of such continuous ranges such that each continuous range belongs to a single group. In this way we would divide the population into a set of groups that are effectively indistinguishable from a random subset of the whole population, as any large scale patterns are effectively removed. Alternatively, we could save a cookie on the user's computer that is a pseudorandomly generated number in a certain range that is small enough that several users are expected to get the same number. Alternatively, these continuous ranges could for example also be replaced with otherwise defined continuous n-dimensional extents and/or be non-uniquely mapped to a certain group with a similar effect for the purpose of the invention, i.e. that of creating a suitable locality-sensitive hashing.

Stochastic group assignments will not prevent the hashing method from being applied and can also add a meaningful layer of extra anonymity. Certain data, such as biometric data, usually contains some noise level due to measurement error and/or other factors that makes any subsequent group assignment based on this data a stochastic mapping as a function of the identity. Stochastic elements can also be added on purpose. For example, the system may simply roll a dice and assign an individual to a group according to a deterministic mapping 50% of the time and assign the individual to a completely random group the other 50% of the time. The data can still be used in our system as long as the distribution of this stochastic assignment is known and/or can be estimated. Further, the simple dice strategy above will be roughly equivalent to a k-anonymity with k=2 in addition to the anonymity already provided by the grouping.

Examples—Noise-Based Anonymization

Some aspects of the invention comprise a noise-based anonymization module. A noise-based anonymization module generates a new noise-masked identifier based on the identifying data. Such a module uses a stochastic mapping where the output is irreversible due to the added noise rather than by limiting the amount of information stored. In other words, the signal is kept below the identifying limit even if the total amount of information used to store the signal and noise would hypothetically be greater than this limit. Any stochastic mapping can be used such that linking a noise-masked identifier to a specific identity is unlikely. In contrast to a hashing module, the noise-masked anonymization module produces an output with sufficient information content to identify a unique person. However, some part of this information is pure noise added by the anonymizer and the actual information concerning the identity of a person is below the threshold required to link data points on the individual level with high probability. Although a hashing module is preferable in most cases, the noise-masked identifier might match more naturally into noisy identifiers of various kinds and also prevents certain deanonymization in some cases where an attacker knows that the person has been recorded.

Noise can be any external source of information that can be considered noise in the context of the invention and does not imply a source of true noise. For example, time stamps or values from some complex process, chaotic systems, complex systems, various pseudorandom numbers, media sources and similar sources whose patterns are unlikely to be reversible could be used. From anonymity perspective it is important that this noise cannot easily be recreated and/or reversed and the statistical purpose of the invention additionally requires that it can be described by some distribution and does not introduce significant unwanted correlation that alter the statistics.

FIG. 12 is a schematic diagram illustrating an example of how an identifier skew measure can be made anonymous by adding noise at one or more times and how this can generate a bias compensation term. In this example, visitation counters are used for health state A and B, respectively. There population counters are randomly initialized, e.g. before the data collection starts. A bias compensation term is calculated by estimating the population flow from A to B resulting from spurious correlations in the initialization, which can be removed from the population flow estimate in the future in order to lower the variance of the estimate. To further mask the initialization, an additional small noise may optionally be added to the compensation term at the cost of a slightly increased variance in the population flow.

FIG. 13 is illustrating an example of noise-masking anonymization. It shows the probability density function of the noise-masked identifier given some identifier. The probability density functions, in this example approximately normally distributed around the identifier, for two different identifiers are shown. Not all possible input values may correspond to an individual in the population and/or memory. Where the probability density functions from different identifiers are overlapping, the original identity generating that noise-masked identifier may not be known with certainty. Reidentification using a specific noise-masked identifier becomes less probable as more overlap from the probability density functions of various identifiers is provided for that specific noise-masked identifier, for example by having more identifiers in the population and/or memory.

Examples—Anonymized Identifiers

For example, an anonymous identifier is herein considered a group identifier and/or a noise-masked identifier.

By way of example, people devices, etc that are assigned to the same group by the hashing module may be seen as a hash group.

An individual is used in descriptions of the invention to refer to any individual person, identifiable device and/or similar objects that can be considered linked to a person and used to identify a person. For example, mobile phones and network cards can be considered as individuals in the context of this inventions, since tracking these objects allow tracking of individuals.

Examples—Skew Measure

For example, skew of data herein refers to how some particular data is distributed compared to the expectation from the generating distribution. The skew measure is some information describing the skew of the collected data. In other word, the invention measures how the actual identifier distribution differs from the expected identifier distribution, for example the distribution if all individuals were equally likely to visits both health states. It is usually encoded as one or more floating point or integer values. The purpose of the skew measure is to later be compared between health states in order estimate how much of this skew is common between two health states. A large number of varieties of skew measures will be obvious to the skilled person. Practically any skew measure can be used in the invention, although some skew measures preserve more information about the data skew than others and thus are likely to provide a better estimate of the skew.

Note that a skew measure does not necessarily imply that the generating distribution is known, i.e. that enough information has/have been collected about the expectation of the generating distribution in order for the skew to be calculated from the skew measure. However, if the underlying distribution would later become known the skew measure would already contain the information necessary to estimate the skew the data. That said, the result generating distribution will be trivial to estimate if the identifiers are decorrelated, e.g. using a decorrelation module.

The most elementary example of a skew measure is to keep a list of the original visiting group identities or noise-masked identities, together with any associated additional data, which offers anonymity but may be inefficient in terms of storage space as they contain redundant information. However, in some cases, keeping such original anonymized identities allows a better optional post-processing, for example removal of outlies, as well as greater flexibility in changing the skew measures ad-hoc for various purposes.

Another example of a simple skew measure is a visitation counter. Such a visitation counter is counting the number of identities detected at each subject state for each hash group. It could, for example, be a vector with the numbers 5, 10, 8 and 7, representing the number of visiting identities assigned to each of four group identities at a certain health state.

More generally speaking, a skew measure may for example consist of two or more sums and/or integrals over convolutions of: some mapping from the space of anonymized identifiers to a scalar value; and the sum of Dirac or Kronecker delta functions of the anonymous identifiers visiting a health state. In other words, we measure the identifier distribution in two different ways. In the specific case where the anonymous identifiers are discrete, such as an enumeration, and the respective mappings are Dirac delta $d(i)$ for $i=1:n$, this is equivalent to a visitation counter. In other words, a skew measure is a generalization of the anonymous visitation counter. In other words, the skew measure is two or more counts of the number of detected anonymous identifiers from some defined subset of the set of possible anonymous identifiers, where the count may be weighted by any function dependent on the anonymous identifier. Expressed differently:

$$\text{sum}\_i\, f(x\_i)$$

where $x\_i$ is a anonymous identifiers visiting a subject state, $i$ is some index of all anonymous identifiers visiting a subject state and $f(x)$ is some mapping from the space of anonymous identifiers to (not necessarily positive) scalar values.

The above sum can be seen as a density estimate of the visiting subpopulation. Since it estimates the distribution of the actual visiting identifiers, which is a finite and known population rather than a proper unknown distribution, we also use the less common but more precise term "density measure" herein to describe such quantities. The simplest density measure is a count of total visits, corresponding to equal weighting across identifiers, which could be used together with another density measure to arrive at a very simple skew measure. In the preferred embodiment a hundred or more density measures would be used as a vector-valued skew measure.

Alternatively, a skew measure may consist of information representative of one or more difference between such density measures. For example, given two counts we may simply store the difference between them as a measure of the skew. In other words, the skew measure is generally a vector-valued data that consists of information representative of the skew of the identifiers in comparison with the expected distribution of all identifiers sampled from some larger population.

This information may be encoded in any way. Although the method could theoretically work with only a single difference between two density measures, it is most often preferable to rely on as large a number of density measures as the desired level of anonymity allows in order to reduce the variance of the population. In the preferred embodiment of the hashing module, 10-1 000 000 000 density measures are used, depending on how large the group of potential visiting identities are and the expected size of the dataset. From another perspective, reaching an average anonymity level roughly equivalent to k-anonymization with $k=5$ is almost always desirable and a stricter $k=50$ or more is recommended in most cases.

A key realization to the utility of the method is that the flow measures can surprisingly reach a very low variance using a large number of density measures and/or other information-rich skew measures, while still preserving the anonymity of the individuals. An extremely low number of density measures will be impractical for the stated purposes due to prohibitive variance, but this disadvantage disappears as the skew information encoded in the skew measure, e.g. the number of density measures used, increases.

For example, a visitation counter for two or more tempo-spatial locations, also referred to as spatio-temporal locations, may be used. This keeps track of how many times people from each of two or more hash groups have been detected at a tempo-spatial location, for example: a certain web page, a specific street, in a certain store and so forth at a certain time (recurring or unique).

A more general skew measure than visitation counters is, as mentioned above, a set of identifier density measures, also called density measures herein. A density measure indicates the density of identifiers in the data according to some weighting. For example, a skew measure could be a set of Gaussian kernels in the space of possible identifiers. Specifically, the density measure associated with each kernel may include sums of the weighted distances, i.e. a Gaussian function of the distance, from the center of the kernel to each anonymized identifier. Two or more such density measures from different Gaussian kernels, or one or more comparisons between such density measures, would then represent a skew measure. An identifier density measures can measure the identifier density of identifying data and/or anonymous data.

Such density measures can be correlated between the two points just like the visitation counters used in some of the specific examples described herein in order to estimate the population flow. This is true even if the density measures are different, for example if different density measures are used in point A and B. For example, the same method that may be used for visitation counters, i.e. of establishing a minimum and maximum expected correlation depending on the number of coinciding visitors using Monte Carlo and/or analytical estimation.

For the purpose of providing anonymity it is important that this anonymization into an anonymous skew measure takes place effectively online (or in real-time and/or near real-time), i.e. continuously with but a short delay between the acquiring of the identifier and the generation and/or updating of the skew measure. In the preferred embodiment the hashing takes place inside a general-purpose computer being located in a sensor system or a general-purpose computer immediately receiving this value. The value should not be able to be externally accessed with reasonable effort before being processed. Immediately after processing the identifier should be deleted. However, if needed the data may be batched at various points and/or otherwise handled over some small time interval (for example transmission in nightly batches) in the preferred embodiment if this extended type of online processing is necessary for reasonable technical requirements and if it is also not considered to substantially weaken the provided anonymity of the subject. In contrast, offline methods are generally applied after the whole data collection has been completed. Such offline methods cannot be considered anonymous due to the storage of personal data.

Subject States and Visits

The group identities, noise-masked identities and other skew measures, for example visitation counters, and/or any data tied to group identities and/or noise-masked identities, may optionally be modified in any way, for example by removing outliers, filtering specific locations, filtering group identities that coincide with known individuals, or by performing further microaggregation of any data.

Health state, also referred to as health-related subject state, is any description of a person's health, medication, health monitoring, treatments and/or health-related aspects of his/her lifestyle. In other words, the subject state is some category describing the persons health either in him/herself of in relation to the interaction with some other entity.

A visit is the connection of an identifier to a health state. For example, it could be an identifiable person being detected in a specific area at a certain time, an IP address filling a health-related web form or a subject being tested for a disease. Tempo-spatial aspects of health states herein refers to any health-related extent, not necessarily continuous, in space and/or time. It can, for example, be the number of visits to a certain hospital on any Friday morning. The count can be any information about the number of individuals. For example, it can simply keep a Boolean value that keeps track of whether at least one individual has visited a tempo-spatial location or not. In another example, it can keep track of how many more individuals from a certain group have visited compared to an average across all groups. It can also keep track of more specific location data, for example specific geocoordinates and time stamps, that is at some later point aggregated into larger tempo-spatial locations, .e.g. a vicinity of a chemical plant. This specific data is then considered keeping track also of visits to the larger locations implicitly. One example of a possible visitation counter is illustrated in FIG. 4.

A health state may be related to any population somehow defined and being of interest to a study of health transition. It may, for example, be defined as: people living in a certain area, people admitted to a certain hospital on Fridays, people using a smart health monitor with high heart rate, people with certain syndromes, people volunteering to a study and/or other similar such categories that could be of interest to a health study. In additional examples, any combination of health status, diagnosis, treatment, intervention, monitoring, syndrome, test results, sensor data ranges, localisation and/or time may be used to define health states. The counter itself keeps track of how many people from each of two or more group identifier that are in that health state. This can, for example, be a relative number, as in a percentage of individuals, and/or an absolute number of individuals. It can be stored in a variety of ways, for example as a vector or as a number of database entries with anonymized identifiers indicating to which group identifier the entry belongs. Also, counters encoding information about the number of people in other ways may be used, such as a Boolean value indicating if the number of people in the group is higher than average or higher than a set threshold. Many other ways to encode the information such that information about the number of people per group identifier per health state can be extracted is obvious to the skilled person. Subject states can also be defined with fuzzy logic and similar partial membership definitions. This will generally result in partial visits rather than integer values and is generally compatible with the invention.

Examples—Anonymous Population Flow Estimation

The flow measurement uses the data from the skew measure to measure the transition and/or flow of individuals from one health state (A) to another health state (B). Since each hash group and/or density measure represents a multitude of individuals, we cannot know precisely how many people from a certain group or population present in A that were also present in B. Instead, the invention exploits higher order statistics to generate noisy measurements.

The measure of the flow is an estimate of the amount of people that visit both health state A and B in some way. For example, it may be the amount of people transitioning from state A to B and/or the percentage of the number of people transitioning from A to B. It can also be, for example, to measure the amount of people visiting A, B and a third health state C (where the people also visiting C can then be seen as a subpopulation for the purposes of the invention). In another example, it can be the number of people visiting A and B, regardless of which subject state is visited first. There are many varieties of such measures available. The number of people visiting A together with the number of people visiting B, independent of any correlation between the corresponding identities between the subject states, is not herein considered a population flow estimate but rather two population estimates corresponding to two locations.

The identities of subjects visiting a subject state will be skewed compared to the estimated visitation rate from all individuals in some hypothetical larger population due to the fact that the visiting individuals form a subset of all individuals in the larger population. If the same individuals are visiting state A and B, this can be measured using the corresponding skew measures. Such a measure is complicated by the fact that we do not necessarily know the theoretical underlying distribution of visitors to A and B. For example, A and B may display similar data skew due to phenotypes in the geographic area, if biometric phenotypes are used, or due to the fact that the visitors have similar phone brands with corresponding MAC-ranges, if MAC-addresses are used. Such correlations will be difficult or impossible to isolate from the coinciding visitors.

Some types of identifiers are, truly and/or approximately, randomly and independently assigned to individuals in a population, e.g. if a random number is picked as a pseudonymous identifier. Such identifiers will display no data skew between A and B due to causes other than that of the individuals coinciding between the locations. In other words, the estimated distribution of the hypothetical larger population is known. In other words, the identities are then effectively independently sampled for each individual and the distribution of the assignment is known. This means that the precise expected distribution of identifiers in A and B is known. Since the expectation is known, the skew from this expectation can also be estimated without need for data collection and with no resulting bias. Moreover, the independence of the identifier assignment also means that a skew measures such as the specific ones discussed above, i.e. weighted sums and integrals that depend linearly on each detected identity, will become analytically derivable mappings of the number of coinciding individuals.

For example, practically any scalar value that depends linearly on the skew measure can be used for constructing a flow estimate if the mapping is linear. It will also be straightforward to estimate this linear value, e.g. using Monte Carlo methods or analysis, for the specific case of a some maximum correlation between individuals in health state A and B respectively as well as for the specific case when the individuals in the two subject states are different individuals. Due to the independence of the identifiers the flow estimate can easily be constructed using a linear interpolation between these two values. The preferred embodiment uses a correlation between two identical types of skew measures for simplicity.

Note that the population flow measure, depending on its form, e.g. questions such as if it is stated as percentage of visitors and/or total amount, might depend on the total or relative number of individuals in A and in B, which in this case might also need to be collected for each health state.

Any nonlinear case would require more analytical footwork in its design and might be computationally more expensive, but is otherwise straightforward and will be equivalent in function. The preferred embodiment is linear due to its simplicity and efficiency.

Many types of identifiers, however, are not even approximately randomly assigned, for example home address geo-location data. They may for example correlate with the frequency to visit a health state a priori. In these cases, the invention can optionally use, for group identifiers, a decorrelating hashing module and, for the noise-masked identifiers, a decorrelation module, in order to remove any unwanted correlations present in the identifier distribution and make the identifiers approximately independently generated from each other and functionally equivalent to a random and independent assignment. Once this has been done a flow measure, such as a linear transform, can easily be constructed without prior knowledge about the initial distribution as described above.

Concrete examples and preferred embodiments of the generation of population flow estimates can be found in the various examples below.

In the preferred embodiment, a baseline is established by estimating, for example by dividing the total number of visits for all groups in the visitation counter with the number of groups, the expected number of visits per group. Such an expectation baseline may also contain a model of the bias, e.g. in case the expected bias by sensor systems and/or similar that are used in directly or indirectly in generating the anonymous identifier can be calculated by depending on factor such as location, recording conditions and time of recording. Additionally, the baseline may be designed taking into consideration population behavioural models, for example: the tendency for repeated visits to a location per individual and/or the behaviour of visitors that are not recorded for some reason. By subtracting this baseline, the preferred embodiment arrives at the skew of the data per group. By way of example, skew of data may refer to how some particular data is distributed compared to the expectation from the generating distribution.

For example, the correlation between the variances per group in A and B represents the skew of the joint distribution. A careful consideration by the inventor reveals that a measure of the number of individuals can be achieved by exploiting the fact that the group identity and probability of an individual to go from A to B can effectively be considered independent and identically distributed, which may be guaranteed through the design of the hashing module and/or decorrelation module. For example, by relying on the assumption of the independence attribute and by using: knowledge of the stochastic aspect of the distribution of the hashing module (which may include models of any sensor noise, transmission noise and other factors involved), if applicable; and a behavioural model that describe the distribution of the number of visits per individual etc, we can create a baseline skew of the joint distribution (for example a Pearson correlation coefficient identical to 0) that would be expected if the two populations visiting A and B were, from a stochastic perspective, independently generated. We can also, using a similar behavioural model and/or knowledge of the stochastic distribution in the hashing module, estimate the skew of the joint distribution in case the two populations consisted of exactly the same individuals (for example a Pearson correlation coefficient equal to 1). For example, such a skew for perfectly coinciding populations may be adjusted based on models of sensor noise, wherein the sensor noise model can be dependent on other factors, such as sensor noise models, location, group identity, identifier noise and/or knowledge of the stochasticity in the hashing process. In a simple example with homogenous groups, comprising a hashing module with 50% chance for consistent group assignment for each individual (with otherwise random assignment between all groups) could double the population estimate for the same skew compared to the estimate for a 100% accurate hashing module.

A statistical measure of the number of individuals can then be generated by for example performing a linear interpolation between two such extremes based on the actual skew as measured by comparing the skew measures. Note that these steps are only an example, but that the independence assumption will result in the population flow measurement being representable as a linear transform, such as the one indicated in some aspect described herein. Various specific embodiments and ways to design specific such embodiments can be arrived at by the skilled person from this and other examples and descriptions herein.

In certain cases, the identifiers are decorrelated already from the beginning. This may, for example, be the case with unique identifiers, for example assigned through cookies or to devices and cards, where the identifier is a truly random or approximately random number generated for each individual.

The complexity in generating such a measure without the decorrelation assumption made possible by the inherent design of the hashing module, and with noise-masked identifiers by the decorrelation module, would in many cases be prohibitive. Note that this simplification does not only simplify the precise design process of the embodiments, but will also result in cheaper, faster and/or more energy efficient methods and systems due to the reduced number of processing operations being reduced and/or simplification in the hardware architecture required.

The groups in this example do not necessarily need to be of the same distribution (for example having identical estimated group sizes) a priori. With different expected group sizes, the population flow estimation will affect the estimated value per group counter and the (normalized) correlation in a straightforward manner. Any related estimation of variance for the population flow measure might become more convoluted, for example as any Gaussian approximation of the distribution of correlations might be invalid if the group differences are large. Likewise, the density measure and/or other skew measures may differ in a multitude of ways.

More complex health states may for example also be defined in order to calculate refined population flow estimates. An identifier skew measure, such as a group identity may for example be stored together with health state as above (i.e. with an "original" health state) and the ordering of the visit (i.e. an ordinal), which then allows calculation of the population flow from original health states before and/or after each particular visit of the health to an original state. This can from the perspective on the invention be viewed as an aggregation of many individual new health states (i.e. one subject state per ordinal and original health state) into a larger health state (i.e. states before and after a particular visit) together with the aggregation of population flow estimates into larger population flow (i.e. the population flows from all health states before a particular visit x in state B, summed over all recorded visit x in state B). This more complex calculation allows the calculation of the population flow to B from A with a lower variance, but the larger number of health states leads to a smaller number of anonymized identities in each health state, which might weaken the anonymity provided by the invention.

Examples—Locality-Sensitive Hashing

Correlations in the anonymized identifiers can usually, but not always, be avoided through decorrelation. A particular case of where it cannot usually be avoided is with certain noisy continuous identifiers. For example, continuous measurements of biometric data can be hashed using a locality-sensitive hashing (LSH), which allows continuous measurements that contain sensor noise to be used in microaggregation for our purposes. Such a hash function can be approximately and/or effectively, but not perfectly, decorrelating. Any choice of a specific LSH necessitates a balance between its decorrelating properties and its locality-preserving properties. Even if such hash is largely decorrelating the data it is still likely to preserve some remaining small bias in the distribution of the hash resulting from any correlation between biometric measurement and a priori tendency to visit a location (if such correlations are at all present in the original continuous distribution). A term in the baseline("err"), further elaborated on below, may then be used as a compensation of such remaining correlations. Note that we do not strictly use decorrelation such as that from the avalanche effect in this setting but assume that small scale correlations resulting from the locality-sensitivity have a small effect on the resulting statistics (in other words, the correlations are effectively removed). In particular, any significant correlation between the data and a priori tendency to visit a location is likely to be a large-scale pattern. LSH-based hashing modules are not limited to continuous data, but could be utilized for other data, for example integer values, as well.

As a particular example of LSH, a locality-sensitive hashing may be designed by splitting the space of continuous identifier values into 30 000 smaller regions. A cryptographic hash, random table and/or other method may then be used to effectively randomly assign 30 regions to each of 1000 group identifiers. This means that two effectively independently sampled noisy continuous identifiers received from an individual have a large probability of being assigned to the same group. At the same time, two different groups may be likely to have a negligible difference between them due to each group consisting of 30 independently sampled regions of the feature space. The decorrelation will generally be effective if the regions are much smaller than the correlation patterns of interest. For many well-behaved continuous distributions, both the noise resistance, i.e. robustness of the variance of the population flow estimate to the presence of noise such as identifier/sensor noise etc, and the effective decorrelation of the groups can be achieved at the same time. Since an individual may be assigned to different regions solely due to the noise in the identifying data it may beneficial to compensate the estimation for the resulting stochasticity in the group identity assignment.

As an example of the above concepts concerning LSH, people over 120 cm of height may be significantly less likely to enter a toy store than those under 120 cm, while the corresponding a priori difference between people whose height is 119.5-120 cm and people between 120.0-120.5 cm of height is likely to be negligible and hence approximately uncorrelated.

Note that the decorrelation module might also use an LSH as described above in order to produce a locality-preserving identifying value with effectively no correlations of the type described above. The difference compared to a anonymizing module is that the number of possible decorrelated identifier values is sufficiently large for an individual to be uniquely identified from the value. For example, the collision probability of a decorrelating hash may be low. There might be some resulting probability of failing to identify a person correctly, but not sufficiently to be considered anonymizing (i.e. the decorrelation module decorrelated but does not anonymize). Stochasticity then becomes a necessary additional anonymization step to the LSH in order to protect the personal identify.

It can be noted that for large number of sample and a large number of possible hashes the correlation of two independent populations are approximately normally distributed. This makes it easy to also present confidence intervals for generated measures if desired.

Examples—Behavioural Models

The population flow may optionally be modified by a behavioural model in order to arrive at derivative statistics, such as the flow of unique individuals if visits can be repeated at each location. Such a behavioural model, could for example estimate the expected number of revisits per individual. Such a behavioural model could also, for example, be estimated together with the population flow iteratively in an estimation-maximization process where the population flow and behavioural models are repeatedly updated to improve the joint probability of the observed identifier distributions.

Example Implementation

In an example preferred embodiment a server in the example system applies a hashing module to received identifiers and stores an integer between 1 and 1000, effectively random due to the avalanche effect. Assuming the number of individuals to be 10000 assigned to health state A and B respectively and assuming individuals only go once per day in one direction and with no other correlation between the corresponding populations at A and B, the expected mean for both points is 10000/1000=10 individuals per group. We may encode the measured number of individuals per group in integer valued vectors n_a and n_b respectively. We can now calculate the unit length relative variance vectors v_a and v_b as v_a=(n_a−10)/norm(n_a−10) etc (where the function norm(x) is the norm of the vector and subtracting a scalar from a vector signifies removing the scalar value from each component). Assuming that every individual passing A also passes through B in a day we arrive at a perfect correlation, E[v_a*v_b]=1 (where * is the dot product if used between vectors and E[ ] is the expectation). Instead assuming that the population in A and B always consist of different individuals, we can instead estimate a baseline as E[v_a*v_b]=0, here using the uncorrelated assumption made feasible due to the use of a hashing module. Assume now that the number of individuals at B, c3, consist of two groups of individuals, c1 (with relative variance vector v_a1) coming from A and c2 (with relative variance vector v_a2) not coming from A. The expected correlation in this case becomes E[c3*v_b*v_a1]=E[(c1*v_a1+c2*va2)*v_a1]=c1. This means we can measure the expected number of individuals going from A to B as nab=v_b*v_a1*10000. Assuming we measure a scalar product of 0.45 between v_b and v_a in this example we arrive at a measure of 4500 individuals, or 45% of the individuals in B, coming from A. In other words, we arrive at an unbiased measurement using strictly anonymous microaggregated data that can be implemented as a linear transform through the use of a decorrelating hashing module. The data generated by the hash module in the example may be considered anonymous and uploaded to any database without storing personal data. The described calculations herein can then preferably be performed on a cloud server/database through the use of lambda functions or other such suitable computing options for the low-cost calculations required to perform a linear transform.

The counters and/or correlation may be normalized or rescaled in any way as part of generating the estimate. The various calculations should be interpreted in a general sense and can be performed or approximated with any of a large number of possible variations in the order of operations and/or specific subroutines that implicitly perform effectively the same mapping between input and output data as the calculations mentioned herein in their most narrow sense. Such variations will be obvious to the skilled person and/or automatically designed, for example by compilers and/or various other systems and methods. In case of a slightly imperfect hash function the resulting error in the above assumptions can be partly compensated for by assuming $E[v\_a2*v\_b]=err$, where err is some correlation in the data that can be estimated, for example empirically by comparing two different independent samplings from the population (i.e. measuring traffic at two spots that can have no correlation with each other). The expectation then follows the following equality: $c1=E[(c1*v\_a1+c2*va2)*v\_b]-err$. This err term may for example be used as a baseline or part of a baseline.

Note that this simple case is slightly more complex when the number of people in A is greater than in B. Even if all people in B come from A we would expect a less than ideal alignment in the group distribution. This maximum expected scalar product could easily be estimated from the total number of visits to A and B. In these cases the linear transformed used to arrive at the estimate becomes a function of the total number of visits in A and B, respectively.

If a noise-masked identifier is used we could simple divide the identifier space into a number of areas and calculate the density estimation for each. A calculation can be performed for these density measures that is analogous to the visitation counters above.

Examples—Anonymizing Skew Measures

An issue that can arise using any skew measure is that the health states are initially weakly populated by visits and that a probabilistic linking of an identity to a multitude of data points is then possible for an attacker if the identifier is known.

For example, a visitation counter might have a group with a single visit to health state A, then it might be reasonable to assume that an individual is the only registered individual from that group in the dataset or, more specifically, reasonable to assume that he/she is the sole individual in A.

Alternatively, it might for example be reasonable to deduce the group identifier from sparsely populated data in a given location, e.g. a known home address. It can then be checked against and a work address, In that case it might be possible to infer that he/she was indeed present at location B with a high probability. This specific case can be countered by only storing the skew measure in location A and generate the population estimate online, i.e. updating it with every single visit to B using the skew measure from A, but without storing the skew measure from B. However, this method will be ineffective if the population flow estimate from B to A also needs to be calculated.

A solution for these weakly populated states, as well as a potential anonymization solution in its own right, is to use anonymizing skew measures.

Anonymizing skew measures work by adding a degree of noise to the stored skew measure. This can for example be done before starting the data collection, as well as at during any number of moments during the collection. This noise could potentially bias the population flow estimate. The bias can be compensated for by calculating the resulting bias based on the estimate of the noise. More problematic is that this will also increase the variance of the population flow estimate.

An optional improved mechanism can be designed. In this mechanism, the bias generated from the specific noise sample used, and/or other information suitable for generating such a bias based on the specific noise sample, is also generated. For example, a random number of "virtual" visits per group identifier can be generated and prepared for addition to a visitation counter. The total population flow estimated from A to B by the spurious correlation of all such virtual visits in A and B is also stored as a bias term, as well as the number of total virtual visits per location. Since the correlation from the actual generated virtual visits is precisely known at the moment they are generated, it can also be calculated and removed precisely through the bias term. This method significantly reduces the variance in the data, although some cross terms caused by spurious correlations between actual visits and virtual visits may remain as a contributor to the variance. Instead of storing a bias term directly, any information necessary for generating such could alternatively be stored. If too much information about the noise is stored, the data might be deanonymized. However, the necessary bias term is a single value, while the noise is typically vector-valued, so there are many possible ways to store sufficient data without storing enough information about the noise to deanonymize the data.

In the particular illustrative example of a visitation counter encoded in a vector v_a and v_b, we have:

$$v\_a = f + a + n\_a$$

$$v\_b = f + b + n\_b$$

where a and b are the visits and/or assignments unique to health state A and B, respectively, and f the common population. n_a and n_b are noise terms.

In this example, various measures of population flows are related to the following value:

$$E[v\_a'*v\_b] = E[f'*f] + 2E[(a+b)'*f] + 2E[a'*b] - 2E[(a+f)'*n\_b] + 2E[n\_a'*(b+f)] - n\_a'*n\_b'$$

where * is the dot product and ' is transpose of the vectors.

Note that if the noise level is substantial the direct calculation of the noise terms rather than its estimation might reduce the variance significantly and so in particular if the variance in the noise is larger than the variance in the other terms, for example if the visitations counters are sparsely populated. The mixed noise/data terms such as $a'*n\_a$ can also be calculated precisely if the noise is added after the data, or partially calculated and partially estimated if the noise is added at some point during the data collection.

As a final security measure, a small amount of noise may be added to the compensated bias term generated from the virtual visits. Usually a very small random number, such as between 0 or 1, is sufficient to mask any individual contribution to the skew measure even in exceptional cases where such can be isolated from the skew measure Such noise to the bias term might prevent reconstruction of the skew measure noise when a larger number of health states are used. Optionally, the noise is sufficiently high that no precise number of visits for any identities is deducable with a probability higher than 0.5. For example, if the noise is generated based on a random integer number of visits per group identifier, the probability of any such specific number of visits per group identifier should then ideally be 0.5 or less.

Practical memory storage limitation usually limits the noise range that can be used. However, this is more of a theoretical concern if the probability is higher for generating small values and progressively smaller for larger noise additions. This lacks any effective maximum value, except with a probability that is negligible. For example, probability density functions exponentially decaying with the magnitude of the noise might be used. Such noise preferable has an expectation value of 0, in order to avoid reaching high values with multiple additions of noise. In other words, $$p(x)=k1*\exp(-k2x)-k3$$

for some constants k1, k2 and k3 and with x greater than or equal to 0.

The stored number virtual visits per health state can be used to remove such when calculating population flows in percentages and the total number of visits.

Addition above is in the general sense of generating a new skew measure based on the skew measure and noise, but actual addition is preferable due to its ease of isolation into a bias term for later exact correction.

Skew measures rendered anonymous by addition of noise may be considered sufficient to provide anonymity without the use of an anonymization module. This is also true even if the noise is only used once as initialization before the data collection. A weakness is that if the anonymized data can be accesses at two points in time, then the number of visits for any specific individual between those moments can trivially be extracted.

Another alternative is to add such noise after every visits. The resulting methods are then more or less equivalent to a noise-masking anonymization module. Note that the method described above of generating a precise correcting bias in the population flow estimate, using the momentary knowledge of the noise, can also be applied to a noise-masking anonymization module and/or hashing module.

In case of continuous skew measures, such as storing precise continuous identifiers, the method may also be used. Such noise in the skew measures may for example be generated based on a sufficient amount of virtual visits for an individual visit to be indistinguishable.

The preferred embodiment for most applications is a combination of methods with an initial anonymizing noisy skew measure with a stored bias correction term generated from the specific noise sample in combination with skew measures generated by a hashing module, for example a group identifier counter. If accuracy of the population flow estimate is more important than anonymity, then relying only on a random initialization of an identifying skew measure may be more appropriate to reduce the variance.

A disadvantage of all noise-based methods is that true noise sources may be scarce and that many sources of pseudorandom noise can be reversed, which would significantly simplify an attack on the anonymization.

On the mechanical level, such anonymized skew measured are generated by the anonymization module, typically online, in part by the received identifier and in part by the identifier skew measure already stored in memory. The noise can be added by the anonymization module and/or by a separate mechanism that adds noise to the memory. Each new identifier skew measure generated based in part on such a noisy identifier skew measure may then be rendered anonymized provided that the noise level is sufficiently high.

Examples of Applications

In the following, a non-exhaustive number of non-limiting examples of specific technological applications will be outlined.

Anonymously Tracking and/or Analysing Health Change and/or Outcome of Subjects/Patients.

Another example concerns health monitoring and/or analysis, and especially tracking and/or estimating or measuring transition between health states and/or methods and systems and computer programs for enabling such estimation.

A transition may refer to any assignment to two different health states. This can be assignment to a health state defined as people in a certain region that have been diagnosed with a certain syndrome and an assignment to another health state defined as people that have deceased in that region. Transition does not necessarily imply change in health. It can, for example, be the assignment to a group of healthy individuals in year 1 and assignment to a group of healthy individuals in year 2, i.e. if the invention is measuring how many people stay free from disease in a certain population by default and/or after some intervention. Transition can, for example, also be in/out of groups, i.e. that they no longer belong to any of the studied health groups under treatment after year 1. The non-studied group can then be viewed as an implicitly defined health group. Transition also does not necessarily imply that the two health states have a simple separation in time. For example, the transitioning from a health state defined as being diagnoses with a certain disease and the health state of being cured from the disease can be measured in a population for two years without having any separation in time between the two groups. In other cases, the temporal direction of the transition may, for example, be undefined and/or different for various individual in the group (e.g. having no separation between people first eating chocolate and then becoming allergic and people first being allergic and then starting to eat chocolate in a study if chocolate influences allergy).

The spatial aspect of health state can also be virtual extents of IP addresses, domain names, frames or similar aspects describing the connection between a person to part of the state of an electronic device and that describes the state of his interaction with it.

In the following, a non-exhaustive number of non-limiting examples of specific technological applications for such health monitoring will be outlined.

1. Anonymously comparing effectiveness of two different treatments. People volunteering to a study can be randomized into two groups, each being assigned a different treatment administered by a specialist. Their social security number is hashed into a group id and added to a group identifier counter. Three months after treatment their response to the treatment is recorded by a different specialist as one of five different categories. For each category the identity of the patient is again hashed and the result added to a group identifier counter.

By studying the correlation between the initial treatment groups and the outcomes the effect of each treatment can be studied blindly and fully anonymously without storing any personal data about the patients.

2. Anonymously comparing and/or studying the effect of diet on cardiac disease. A questionnaire describing several variables describing the intake of various food types and cooking oils are sent by health authorities to all inhabitants in a city encoded with pseunonymous identifiers matched against a registry. When returned to the health authorities social security number is retrieved from the registry and hashed into a group id without human intervention. Ten years later the possible responses to the questionnaire are divided into five types of diets. The social security number of all patients seeking treatment at hospitals in the city and all people diseased in the past ten years is hashed into group identities. For each diet type a group identifier counter is created and compared against the group identifier counter from the patient and the diseased and the correlation between diet on hospital treatment rates and mortality is estimated anonymously. The raw estimate is then corrected for the response rate to the questionnaire, the age distribution and immigration and emigration numbers in order to achieve a smaller bias.

3. All wearable devices of a certain model that measures health variables have a unique MAC address. This MAC address is hashed into a group identifier and certain patterns describing the patient's heart function and step counter is uploaded to the key together with the group identifier. All data is time stamped.

The step counter is sent regularly. Over time it is possible to deduce, with the methods described herein, how the heart function changes into different patterns depending on the step count over 1, 2 and 3 months. This can further be divided into subpopulations depending on the starting pattern of the heart of the user. These combinations can be structured into a matrix form and used to create a Markov model that can guide exercise for a patient month-by-month.

4. Patients volunteer to a double-blind placebo-controlled study. Group identities are generated using their social security number. Each group identifier is assigned a batch of either medication or placebo, with the contents unknown to both patients and their caretakers. Three years later, half the group identifiers are randomly assigned to a rehabilitation treatment. Five years later, their social security number is again transformed into a group identifier and stored in a database together with details of their general health. The effect of the medication can easily be estimated by comparing groups that received treatment compared to other groups. At the same time, we can see the effect of rehabilitation both on the medicated group and the placebo group.

In this example, the effect can be estimated even if, for example, the population studied at year five also contains other people not participating in the study.

5. In another example the effect of diet on cardiac disease is studied. A questionnaire describing several variables describing the intake of various food types and cooking oils are sent by health authorities to all inhabitants in a city encoded with pseudonymous identifiers matched against a registry. When returned to the health authorities social security number is retrieved from the registry using the pseudonymous identifier and hashed into a group id without human intervention. Ten years later the possible responses to the questionnaire are divided into five types of diets. The social security number of all patients seeking treatment at hospitals in the city and all people diseased in the past ten years is hashed into group identities. For each diet type a group identifier counter is created and compared against the group identifier counter from the patient and the diseased and the correlation between diet on hospital treatment rates and mortality is estimated anonymously. The raw estimate is then corrected for the response rate to the questionnaire, the age distribution and immigration and emigration numbers in order to achieve a smaller bias.

6. In another more complex example, data concerning blood pressure is autonomously collected using a wearable device on a monthly basis. The blood pressures are divided into enumerable intervals and self-reported diet compositions are reported using a mobile application and classified into a number of categories. The combination of blood level and diet is used as a health state. When self-reporting, the subject takes a picture and a facial recognition neural network is used to produce identifying facial recognition feature vectors. The feature vectors are hashed using a decorrelation module consisting of an LSH enumerating a number of localities greater than the population size in order to produce a decorrelated hash with a high probability of reidentification. The identifier of those subjects who have not consented to use of personal data are then anonymized using an anonymization module. The anonymization module then adds an integer drawn from an approximately Gaussian distribution of integer value to this enumeration, with a modulo operation applied if the number is greater than the maximum population, i.e. generating a type of noise-masked identifier. The Gaussian distribution is chosen so that the distributions per original integer are overlapping and identification using the noise-masked identifier unlikely. The noise-masked identifier is stored together with the health state and descriptions of the camera type and resolution used to take the photo. A vector counting the number of individuals per noise-masked identifier and subject state is used as skew measure. The maximum and minimum correlation, depending on whether the states have independent populations or coinciding, between two states is then estimated using randomly generated feature vectors uniformly distributed in the feature space, which are supplied to a Monte Carlo-estimation that relies on the decorrelation module, the anonymization module, the consent status and a camera-dependent model of the feature vector noise that is relying on the number of various camera types and resolutions. In other words, the Monte Carlo-estimation is used to produce the parameters for a linear transform that generates the population flow estimates when applied to the actual identifiers. These flow estimates are then used to anonymously, for those subjects who have not consented, study the effect of diet on the development of blood pressure by creating a model of how subjects in each combination of diet and blood pressure flow to various states of blood pressure, with diet not used to distinguish states in this second state, in the coming month.

In each of these examples, multiple assignments of the same individual to the same health state will naively be indistinguishable from multiple assignments from different individuals. As such, if the precise number of unique individuals is desired, a behavioural model may, as an example, be combined with the generated measure. We may for example measure the average number of recurring assignments using a related and/or different method to the one described herein. Such a behavioural model can then be used, for example, as indicated in the more general description, to compensate the transition model by dividing the total number of assignments to a health state by the average number of recurring assignments and so generate a measure of the number of unique assignments. Many other types of behavioural models can also be fitted to the data using the general methodology described herein and complex behavioural models may result from the combination of several such sub-models.

The whole population may also be divided in subpopulations of interest. For example, patients may be divided into subpopulations, for example such as male/female, age, region, etc, before applying the hashing. Each subpopulation is then considered a separate population being studied for the purposes herein, even if the same hashing function may be shared across several subpopulations. This information can be stored as separate counters, or the additional information can be stored explicitly together with the group identifier.

More generally, the method comprises the steps of:
configuring one or more processors to receive anonymous identifier skew measures generated based on identifiers from detections of individuals to and/or in each of two health states or health-related subject states;
generating, using said one or more processors, a measure of health transition between two health states or health-related subject states by comparing the anonymous identifier skew measures between the health-related subject states;
storing said measure of health transition to a memory.

The health-related subject state may be any subject state of relevance to determining a health change, transition and/or outcome. The measure of health transition is for example any measure of health change/outcome and/or lack of health change/outcome that could for example be of value for determining the potential effect of public health policies, diet, treatment effects, health-related correlations for further studies etc.

In each of these examples, multiple visits by the same individual will naively be indistinguishable from multiple visits from different individuals. As such, if the precise number of unique individuals is desired, a behavioural model may, as an example, be combined with the generated measure. We may for example see the correlation over time between some different times to the same location and measure the average number of recurring visits per visitor. Such a behavioural model can then be used, for example, as indicated in the more general description, to compensate the advertising revenue model by dividing the total number of visits by the recurring visits and so generate a measure of the number of unique visitors. Many other types of behavioural model can also be fitted to the data using the general methodology described herein and complex behavioural models may result from the combination of several such sub-models.

A particular example of a behavioral model to derive unique visitors may be used to compensate for repeated visits in a short interval being more likely. In these cases, visits from the same group within some time interval might be compensated for or filtered. For example, two visits to the same location within 5 minutes might be considered a single visit or some fractional number, such as 0.01 of a visit, according to some approximation of the probability of these visits being two separate identities.

The whole population may also be divided in subpopulations. For example, visitors may be divided into subpopulations, for example such as male/female, age, region, etc, before applying the hashing. Each subpopulation is then considered a separate population being studied, even if the same hashing function may be shared across several subpopulations. This information can be stored as separate counters, or the additional information can be stored explicitly together with the group identity.

These examples above are not exhaustive of the possibilities.

Examples—Implementation Details

It will be appreciated that the methods and devices described above can be combined and re-arranged in a variety of ways, and that the methods can be performed by one or more suitably programmed or configured digital signal processors and other known electronic circuits (e.g. discrete logic gates interconnected to perform a specialized function, or application-specific integrated circuits).

Many aspects of this invention are described in terms of sequences of actions that can be performed by, for example, elements of a programmable computer system.

The steps, functions, procedures and/or blocks described above may be implemented in hardware using any conventional technology, such as discrete circuit or integrated circuit technology, including both general-purpose electronic circuitry and application-specific circuitry.

Alternatively, at least some of the steps, functions, procedures and/or blocks described above may be implemented in software for execution by a suitable computer or processing device such as a microprocessor, Digital Signal Processor (DSP) and/or any suitable programmable logic device such as a Field Programmable Gate Array (FPGA) device and a Programmable Logic Controller (PLC) device.

It should also be understood that it may be possible to re-use the general processing capabilities of any device in which the invention is implemented. It may also be possible to re-use existing software, e.g. by reprogramming of the existing software or by adding new software components.

It is also possible to provide a solution based on a combination of hardware and software. The actual hardware-software partitioning can be decided by a system designer based on a number of factors including processing speed, cost of implementation and other requirements.

FIG. 10 is a schematic diagram illustrating an example of a computer-implementation 100 according to an embodiment. In this particular example, at least some of the steps, functions, procedures, modules and/or blocks described herein are implemented in a computer program 125; 135, which is loaded into the memory 120 for execution by processing circuitry including one or more processors 110. The processor(s) 110 and memory 120 are interconnected to each other to enable normal software execution. An optional input/output device 140 may also be interconnected to the processor(s) 110 and/or the memory 120 to enable input and/or output of relevant data such as input parameter(s) and/or resulting output parameter(s).

The term 'processor' should be interpreted in a general sense as any system or device capable of executing program code or computer program instructions to perform a particular processing, determining or computing task.

The processing circuitry including one or more processors 110 is thus configured to perform, when executing the computer program 125, well-defined processing tasks such as those described herein.

In particular, the proposed technology provides a computer program comprising instructions, which when executed by at least one processor, cause the at least one processor to perform the computer-implemented method described herein.

The processing circuitry does not have to be dedicated to only execute the above-described steps, functions, procedure and/or blocks, but may also execute other tasks.

Moreover, this invention can additionally be considered to be embodied entirely within any form of computer-readable storage medium having stored therein an appropriate set of instructions for use by or in connection with an instruction-execution system, apparatus, or device, such as a computer-based system, processor-containing system, or other system that can fetch instructions from a medium and execute the instructions.

The software may be realized as a computer program product, which is normally carried on a non-transitory computer-readable medium, for example a CD, DVD, USB memory, hard drive or any other conventional memory device. The software may thus be loaded into the operating memory of a computer or equivalent processing system for execution by a processor. The computer/processor does not have to be dedicated to only execute the above-described steps, functions, procedure and/or blocks, but may also execute other software tasks.

The flow diagram or diagrams presented herein may be regarded as a computer flow diagram or diagrams, when performed by one or more processors. A corresponding apparatus may be defined as a group of function modules, where each step performed by the processor corresponds to a function module. In this case, the function modules are implemented as a computer program running on the processor.

The computer program residing in memory may thus be organized as appropriate function modules configured to perform, when executed by the processor, at least part of the steps and/or tasks described herein.

Alternatively, it is possible to realize the module(s) predominantly by hardware modules, or alternatively by hardware, with suitable interconnections between relevant modules. Particular examples include one or more suitably configured digital signal processors and other known electronic circuits, e.g. discrete logic gates interconnected to perform a specialized function, and/or Application Specific Integrated Circuits (ASICs) as previously mentioned. Other examples of usable hardware include input/output (I/O) circuitry and/or circuitry for receiving and/or sending signals. The extent of software versus hardware is purely implementation selection.

It is becoming increasingly popular to provide computing services (hardware and/or software) where the resources are delivered as a service to remote locations over a network. By way of example, this means that functionality, as described herein, can be distributed or re-located to one or more separate physical nodes or servers. The functionality may be re-located or distributed to one or more jointly acting physical and/or virtual machines that can be positioned in separate physical node(s), i.e. in the so-called cloud. This is sometimes also referred to as cloud computing, which is a model for enabling ubiquitous on-demand network access to a pool of configurable computing resources such as networks, servers, storage, applications and general or customized services.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible.

The invention claimed is:

1. A digital healthcare information management and health monitoring system configured to provide health monitoring of a plurality of individual subjects in a population of individuals and preserve anonymity of each of the individual subjects, the digital healthcare information management and health monitoring system comprising:
an input configured to
receive, for each one of the plurality of individual subjects, health data representative of one or more health states or health-related subject states and one or more of (i) at least one treatment, and (ii) at least one medication, and
identify information representative of an identity of the respective individual subject, the information representative of the individual subject being an identifier;
computer-based processing circuitry configured to
receive, for each one of the plurality of individual subjects, the identifying information representative of the identity of the individual subject, and
generate anonymous identifier skew measures based on the identifying information of one or more of the individual subjects, anonymization into the anonymous identifier skew measures taking place effectively online, the anonymization taking place in (i) real-time or (ii) near real-time in the computer-based processing circuitry, the computer-based processing circuitry being configured to immediately delete the identifying information after processing, each of the anonymous identifier skew measures being information representing a skew of the identifying information of the one or more of the plurality of individual subjects compared to an expected distribution of the identifying information in the population of individual subjects;
a memory associated with the computer-based processing circuitry, the memory being configured to store at least one anonymous identifier skew measure determined based on at least one of the generated identifier skew measures,
the computer-based processing circuitry is configured to
receive, from one of (i) the memory, or (ii) directly from the computer-based processing circuitry, a number of the anonymous identifier skew measures, at least one processed identifier skew measure of the number of processed anonymous identifier skew measures for each of at least two health states or health-related subject states of individual subjects of the plurality of individual subjects, and
generate, without using any of the identifying information of the individual subjects, one or more flow measures related to individual subjects passing from one health state or health-related subject state to another health state or health-related subject state based on the received anonymous identifier skew measures, in relation to the one or more of (i) said at least one treatment, and (ii) said at least one medication, the generated anonymous identifier skew measures and the generated one or more flow measures reducing a number of processing operations in the computer-based processing circuitry; and
an output configured to output the one or more flow measures to provide the health monitoring of the plurality of individual subjects to study an effect of the one or more of (i) said at least one treatment, and (ii) said at least one medication, while preserving the anonymity of each of the individual subjects of the plurality of individuals,
wherein the one or more flow measures are generated without requiring additional identifying information at the other health state or health-related subject state and without linking records related to the individual subjects at the one health state or health-related subject state and the other health state or health-related subject state, and wherein the anonymous identifier skew measures are generated based on the identifying information of one or more of the individual subjects using hashing or noise-masked anonymization.

2. The health monitoring system of claim 1, wherein the computer-based processing circuitry is configured to generate each of the identifier skew measures based on one or more of (i) two or more identifier density estimates, and (ii) one or more values generated based on identifier density estimates.

3. The health monitoring system of claim 1, wherein the computer-based processing circuitry is configured to generate the identifier skew measure based on a group identifier representing a multitude of individuals.

4. The health monitoring system of claim 1, wherein the computer-based processing circuitry is configured to generate each of the identifier skew measures using a combination of the identifier and the noise such that a contribution to the identifier skew measure is rendered anonymous due to a sufficient noise level for a visit to a subject state not being attributable to a specific identifier.

5. The health monitoring system of claim 1, wherein
the computer-based processing circuitry is configured to provide anonymity by adding the noise to the anonymous identifier skew measure stored in memory, at one or more moments, for a total contribution from any single identifier to be undeterminable.

6. The health monitoring system of claim 5, wherein information about a generated noise is stored in the memory by the computer-based processing circuitry and used by the computer-based processing circuitry to lower a variance in a population flow measure.

7. The health monitoring system of claim 1, wherein the computer-based processing circuitry is configured to generate a group identifier based on the identifying information of the individual subject to effectively perform microaggregation of the plurality of individual subjects into corresponding groups, wherein the memory is configured to store group identifier counters or visitation counters for each of two or more group identifiers from each of two or more health states associated with the corresponding individual subjects, and wherein the computer-based processing circuitry is configured to receive counter information from at least two of the group identifier counters or visitation counters, and generate one or more transition measures related to the individual subjects passing from one of the health states to another of the health states.

8. The health monitoring system of claim 7, wherein the computer-based processing circuitry is configured to generate a group identifier based on the identifying information of the individual subject by using a hashing function.

9. The health monitoring system of claim 7, wherein the computer-based processing circuitry configured to
generate the one or more flow measures comprises an input module configured to receive the health data, for each one of the plurality of individual subjects, representative of the one or more health states, and
match the health state of the individual subject with a group identifier counter or visitation counter corresponding to the group identifier related to the individual subject, each visitation counter or group identifier counter for each group identifier corresponding to a specific health state.

10. The health monitoring system of claim 1, wherein any two of the stored anonymized identifiers or identifier skew measures are not linkable to each other in which one or more of (i) no pseudonymous identifier links the health states in the stored data, and (ii) a single individual present in one of the health states or the health-related subject states cannot be reidentified in another health state or health-related subject state with non-anonymous probability using the anonymous identifier skew measures.

11. The health monitoring system of claim 1, wherein the computer-based processing circuitry is configured to subtract a baseline corresponding to an expected correlation from two independently generated populations of individual subjects when generating the one or more flow measures.

12. The health monitoring system of claim 1, wherein each identifier skew measure represents the skew of the identifying information of one or more of the individual subjects compared to an expected distribution of the identifying information in the plurality of individual subjects.

13. The health monitoring system of claim 1, wherein the computer-based processing circuitry is configured to generate each of the identifier skew measures based on one or more of (i) two or more identifier density estimates, and (ii) one or more values generated based on identifier density estimates, and
each identifier skew measure represents the skew of the identifying information of one or more of the individual subjects compared to an expected distribution of the identifying information in the plurality of individual subjects.

* * * * *